(12) United States Patent
Shiraishi et al.

(10) Patent No.: US 8,329,771 B2
(45) Date of Patent: Dec. 11, 2012

(54) PHOTOBASE GENERATOR

(75) Inventors: Atsushi Shiraishi, Kyoto (JP); Hideki Kimura, Kyoto (JP)

(73) Assignee: San-Apro Limited, Kyoto-shi (JP)

(*) Notice: Subject to any disclaimer, the term of this patent is extended or adjusted under 35 U.S.C. 154(b) by 253 days.

(21) Appl. No.: 12/921,713

(22) PCT Filed: Mar. 18, 2009

(86) PCT No.: PCT/JP2009/001201
§ 371 (c)(1),
(2), (4) Date: Sep. 9, 2010

(87) PCT Pub. No.: WO2009/122664
PCT Pub. Date: Oct. 8, 2009

(65) Prior Publication Data
US 2011/0028585 A1    Feb. 3, 2011

(30) Foreign Application Priority Data

Mar. 31, 2008  (JP) .................. 2008-093058

(51) Int. Cl.
*C07C 211/63* (2006.01)
*C07D 453/02* (2006.01)
*C07D 487/04* (2006.01)
*C07F 5/02* (2006.01)
*C08F 2/50* (2006.01)
*C08G 77/00* (2006.01)
*C08G 59/00* (2006.01)
*C08G 71/04* (2006.01)

(52) U.S. Cl. .............. 522/50; 522/53; 522/63; 522/65; 540/450; 540/470; 540/500; 546/13; 546/133; 546/134; 564/8; 564/248; 564/281

(58) Field of Classification Search .......... 522/50, 522/53, 63, 65; 540/450, 470–473, 500, 540/504; 544/224, 245, 253; 546/112, 134, 546/133; 564/225, 248, 281
See application file for complete search history.

(56) References Cited

U.S. PATENT DOCUMENTS
7,297,464 B2* 11/2007 Sakurai et al. ............ 430/270.1
(Continued)

FOREIGN PATENT DOCUMENTS
JP      8-211604 A     8/1996
(Continued)

OTHER PUBLICATIONS

Notification of Transmittal of Translation of the International Preliminary Report on Patentability (Form PCT/IB/338) of International Application No. PCT/JP2009/001201 mailed Dec. 23, 2010 with Forms PCT/IB/373 and PCT/ISA/237.
Toshihiro Toyoda et al., "Layered Compounds XXX. Unusual Reaction of Triple Layered Cyclophanes Containing Anthracene Nucleus," Tetrahendron Letters, 1975, No. 37, pp. 3203-3206.

(Continued)

*Primary Examiner* — Susan W Berman
(74) *Attorney, Agent, or Firm* — Westerman, Hattori, Daniels & Adrian, LLP

(57) ABSTRACT

The object of the present invention is to provide a photobase generator capable of efficiently generating amines (tertiary amines and amidine) high in catalytic activity by sensing light with a wavelength of from 350 to 500 nm (especially, from 400 to 500 nm).
The present invention is a photobase generator characterized in being represented by general formula (1) or (2).
$Y^+$ is a quaternary ammonio group of general formula (3) to (5), and $X^-$ is a counter anion selected from among a borate anion, a phenolate anion, and a carboxylate anion.

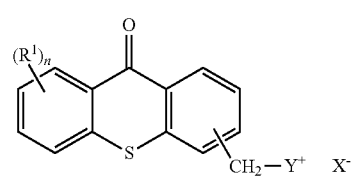

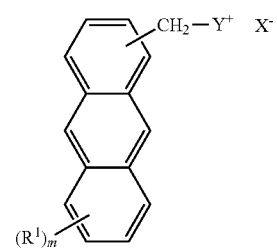

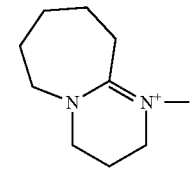

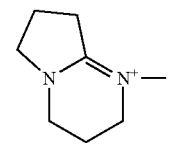

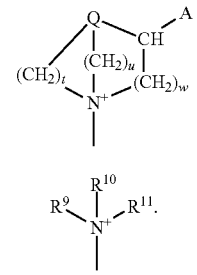

8 Claims, No Drawings

U.S. PATENT DOCUMENTS

| | | |
|---|---|---|
| 7,300,747 B2 | 11/2007 | Okazaki et al. |
| 2009/0071693 A1* | 3/2009 | Tokuhiro et al. ............... 174/250 |
| 2009/0298962 A1* | 12/2009 | Studer et al. .................... 522/46 |
| 2011/0233048 A1* | 9/2011 | Kuramoto et al. ........ 204/157.82 |
| 2012/0095124 A1* | 4/2012 | Kirino ............................ 522/26 |
| 2012/0142806 A1* | 6/2012 | Motofuji et al. ................ 522/53 |

FOREIGN PATENT DOCUMENTS

| | | |
|---|---|---|
| JP | 8-227154 A | 9/1996 |
| JP | 10-007709 A | 1/1998 |
| JP | 2003-195075 A | 7/2003 |
| JP | 2004-077553 A | 3/2004 |
| JP | 2005-107235 A | 4/2005 |
| JP | 2005-511536 A | 4/2005 |
| JP | 2005-264156 A | 9/2005 |
| JP | 2007-119766 A | 5/2007 |
| WO | 98/38195 A1 | 9/1998 |
| WO | 03-033500 A1 | 4/2003 |

OTHER PUBLICATIONS

V. A. Loskutov et al., "Synthesis of 2-Ammonio(phosphonio)methyl-9-oxo-10-(4-heptyl-oxyphenyl)thioxanthenium Bis [hexafluorophosphates(V)]," Russian Journal of Organic Chemistry, Jan. 9, 2006, vol. 42, No. 7, pp. 1097-1100.

Revistade Chimie, 1968, vol. 19, No. 10, pp. 561-565.

International Search Report of PCT/JP2009/001201, mailing date Jul. 7, 2009.

Encyclopedia of Technologies and Materials for Application of Light with partial English translation (compilation).

Kanji Suyama et al., "Quaternary Ammonium Salt as DBU-Generating Photobase Generator," Journal of Photopolymer Science and Technology, 2006, vol. 19, No. 1, pp. 81-84.

Extended European Search Report date of mailing May 3, 2012, issued in corresponding European Patent Application No. 09728259.4.

* cited by examiner

PHOTOBASE GENERATOR

TECHNICAL FIELD

The present invention relates to a photobase generator which generates a base by light irradiation. In more detail, it relates to a photobase generator to be used suitably for the manufacture of a material that is to be cured by the use of a base generated by light irradiation (for example, a coating agent and a coating material) or a product or component to be formed through patterning using a difference in solubility in a developer between an exposed part and an unexposed part (for example, forming materials, layer forming materials, or adhesives of electronic parts, optical products, and optical components).

BACKGROUND ART

A photobase generator which generates a primary amine or a secondary amine (patent document 1 and non-patent document 1) is not suitable as a catalyst for a polymerization reaction or for a crosslinking reaction because of its low activity because the basicity of a primary amine or a secondary amine to be generated is low (i.e., pKa<8). Moreover, there was a problem that a large amount of photobase generator was needed in order to perform a sufficient reaction because these amines have active hydrogen atoms and therefore the amines themselves might react if they are used for polymerization reactions or crosslinking reactions of an epoxide or an isocyanate.

A photobase generator capable of generating a strong base (a tertiary amine, pKa of from 8 to 11) or a super-strong base (e.g., guanidine and amidine, pKa of from 11 to 13) has been proposed so that such a problem should be solved (patent documents 2 to 4 and non-patent document 2).

Moreover, there has been proposed a photobase generator which changes in chemical structure through a photoreaction to generate amidine only when receiving light (patent document 5).

Patent document 1: JP 10-7709 A
Patent document 2: JP 2005-107235 A
Patent document 3: JP 2005-264156 A (U.S. Pat. No. 7,300,747 B2)
Patent document 4: JP 2007-119766 A
Patent document 5: JP 2005-511536 T (WO 03/033500 A1)
Non-patent document 1: Dictionary of Optical Application Technologies and Materials, published by Sangyo-Gijutsu Service Center Co., Ltd., 2006, p. 130
Non-patent document 2: J. Photopolym. Sci. Tech., Vol. 19., No. 1 (81) 2006

DISCLOSURE OF THE INVENTION

Problems to be Solved by the Invention

Although the wavelength of a high-pressure mercury-vapor lamp, which is a light source generally used widely, includes i line (365 nm), h line (405 nm), and g line (436 nm), the photobase generators disclosed in patent documents 2 to 4 and non-patent document 2 have a problem that they exhibit so weak absorption of light especially of 365 nm that they are insufficient in sensitivity.

Moreover, although in the fields of paint and the like, a pigment (for example, titanium oxide) or a binder having an aromatic ring may be blended in a photocurable composition, there is also a problem that such photocurable compositions cannot be cured with conventional photobase generators because the pigment and the binder having an aromatic ring absorb irradiated light (for example, titanium oxide absorbs light of 380 nm or less, and an aromatic ring absorbs light near 365 nm.).

Moreover, the photobase generator disclosed in patent document 4, in which a halogen ion has been used as a counter anion, has a risk of metallic corrosion depending on its intended application. Moreover, the photobase generator disclosed in patent document 5 has a problem that the storage stability of a reactive composition deteriorates if it is contained in the reactant composition because it has basicity also before its chemical structure changes.

The object of the present invention is to provide a photobase generator capable of efficiently generating amines (tertiary amines and amidine) high in catalytic activity by sensing light with a wavelength of from 350 to 500 nm (especially, from 400 to 500 nm).

Solutions to the Problems

The feature of the photobase generator of the present invention is condensed in that it is represented by general formula (1) or (2).

[Chem. 1]

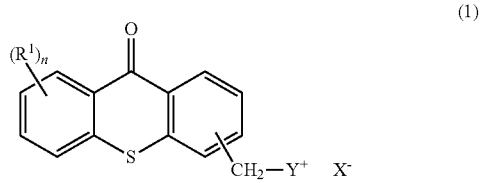

(1)

[Chem. 2]

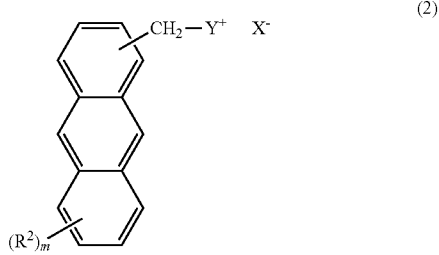

(2)

wherein $R^1$ and $R^2$ are each an alkyl group having from 1 to 18 carbon atoms, an alkenyl group having from 2 to 18 carbon atoms, an alkenyl group having from 2 to 18 carbon atoms, an aryl group having from 6 to 14 carbon atoms, a nitro group, a hydroxyl group, a cyano group, an alkoxy group represented by $—OR^3$, an amino group represented by $—NR^4R^5$, an acyl group represented by $R^6CO—$, an acyloxy group represented by $R^7COO—$, an alkylthio group or an arylthio group represented by $—SR^8$, or a halogen atom, $R^3$, $R^6$, $R^7$, and $R^8$ are each an alkyl group having from 1 to 8 carbon atoms, or an aryl group having from 6 to 12 carbon atoms, $R^4$ and $R^5$ are each a hydrogen atom, an alkyl group having from 1 to 8 carbon atoms, or an aryl group having from 6 to 12 carbon atoms, n is an integer of from 0 to 7, m is an integer of from 0 to 9, $Y^+$ is a quaternary ammonio group represented by any one of general formulae (3) to (6), Q is a nitrogen atom or a methine group (—CH—), t and u are each 2 or 3, w is an integer of from 0 to 2, A is a hydrogen atom, a hydroxyl group, or a halogen atom, $R^9$ to $R^{11}$ are each an alkyl group having 1 to 18 carbon atoms, an alkenyl group having 2 to 18 carbon atoms, or an aryl group having 6 to 14 carbon atoms, $R^1$ or $R^2$ and $CH_2—Y^+X^-$ may be attached to the same benzene ring or alternatively may be attached to different benzene rings, and $X^-$ is a counter anion selected from among borate anions, phenolate anions, and carboxylate anions.

[Chem. 3]

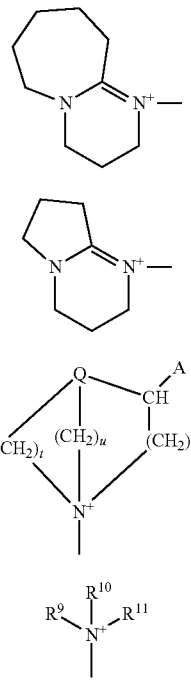

The feature of the curable resin composite of the present invention is condensed in that it contains the aforementioned photobase generator, and a curable urethane resin, a curable epoxy resin, a curable acrylate resin and/or a polysiloxane.

The feature of the method for producing a cured resin (cured product) of the present invention is condensed in that it comprises a step of generating a base by irradiating the photobase generator contained in the aforementioned curable resin composition with light with a wavelength of from 350 to 500 nm.

Advantages of the Invention

The photobase generator of the present invention is capable of efficiently generating an amine having a high catalytic activity (a tertiary amine and amidine) by sensing light with a wavelength of from 350 to 500 nm (especially from 400 to 500 nm).

Moreover, the photobase generator of the present invention does not have a risk of metallic corrosion because it does not contain a halogen ion or the like as a counter anion.

Moreover, since the photobase generator of the present invention does not have basicity before sensitization, it does not lower a storage stability of the reactive composition even if it is contained in the reactive composition.

In addition, since the photobase generator of the present invention is stable also against heat, it hardly generates a base unless light is applied thereto even if it is heated.

Since the curable resin composite of the present invention does not have basicity before sensitization because of the inclusion of the aforementioned photobase generator, the storage stability of the curable resin composite does not fall.

Moreover, according to the method for producing a cured resin (cured product) of the present invention, since the aforementioned photobase generator is used and light with a wavelength of from 350 to 500 nm (especially from 400 to 500 nm) is applied, it is possible to efficiently generate an amine with a high catalytic activity (a tertiary amine and amidine) and therefore it is possible to produce a cured resin (cured product) efficiently.

BEST MODE FOR CARRYING OUT THE INVENTION

A photobase generator refers to such a substance that its chemical structure decomposes when being irradiated with light, so that it generates a base (an amine). The generated base can act as a catalyst for a curing reaction of an epoxy resin, a urethanization reaction between an isocyanate and a polyol, a crosslinking reaction of an acrylate, and the like.

Among $R^1$, $R^2$, and $R^9$ to $R^{11}$, the alkyl groups having from 1 to 18 (preferably from 1 to 12, more preferably from 1 to 8) carbon atoms include linear alkyl groups (e.g., methyl, ethyl, n-propyl, n-butyl, n-pentyl, n-octyl, n-decyl, n-dodecyl, n-tetradecyl, n-hexadecyl, and n-octadecyl), branched alkyl groups (e.g., isopropyl, isobutyl, sec-butyl, tert-butyl, isopentyl, neopentyl, tert-pentyl, isohexyl, 2-ethylhexyl, and 1,1,3,3-tetramethylbutyl), cycloalkyl groups (e.g., cyclopropyl, cyclobutyl, cyclopentyl, and cyclohexyl), and bridged cyclic alkyl groups (e.g., norbornyl, adamanthyl, and pinanyl). As the alkyl group, there can be used, besides the groups listed above, substituted alkyl groups resulting from substitution of some hydrogen atoms of alkyl groups with a hydroxyl group, a nitro group, a cyano group, a halogen atom, an aryl group having from 6 to 14 carbon atoms, an alkoxy group having from 1 to 18 carbon atoms and/or an alkylthio groups having from 1 to 18 carbon atoms.

Among $R^1$, $R^2$, and $R^9$ to $R^{11}$, the alkenyl groups having from 2 to 18 (preferably from 2 to 12, more preferably from 2 to 8) carbon atoms include straight or branched alkenyl groups (e.g., vinyl, allyl, 1-propenyl, 2-propenyl, 1-butenyl, 2-butenyl, 3-butenyl, 1-methyl-1-propenyl, 1-methyl-2-propenyl, 2-methyl-1-propenyl, and 2-methyl-2-propenyl), cycloalkenyl groups (e.g., 2-cyclohexenyl and 3-cyclohexenyl), and arylalkenyl groups (e.g., styryl and cinnamyl). As the alkenyl group, there can be used, besides the groups listed above, substituted alkenyl groups resulting from substitution of some hydrogen atoms of alkenyl groups with a hydroxyl group, a nitro group, a cyano group, a halogen atom, an alkoxy group having from 1 to 18 carbon atoms and/or an alkylthio groups having from 1 to 18 carbon atoms.

Among $R^1$ and $R^2$, the alkynyl groups having from 2 to 18 (preferably 2 to 12, more preferably 2 to 8) carbon atoms include straight or branched alkynyl groups (e.g., ethynyl, 1-propynyl, 2-propynyl, 1-butyryl, 2-butyryl, 3-butyryl, 1-methyl-2-propynyl, 1,1-dimethyl-2-propynyl, 1-pentynyl, 2-pentynyl, 3-pentynyl, 4-pentynyl, 1-methyl-2-butyryl, 3-methyl-1-butyryl, 1-decynyl, 2-decynyl, 8-decynyl, 1-dodecynyl, 2-dodecynyl, and 10-dodecynyl) and arylalkynyl groups (e.g., phenylethynyl). As the alkynyl group, there can be used, besides the groups listed above, substituted alkynyl groups resulting from substitution of some hydrogen atoms of alkynyl groups with a hydroxyl group, a nitro group, a cyano group, a halogen atom, an alkoxy group having from 1 to 18 carbon atoms and/or an alkylthio groups having from 1 to 18 carbon atoms.

Among $R^1$, $R^2$ and $R^9$ to $R^{11}$, the aryl groups having from 6 to 14 carbon groups include monocyclic aryl groups (e.g., phenyl), fused polycyclic aryl groups (e.g., naphthyl, anthracenyl, phenanthrenyl, anthraquinolyl, fluorenyl, and naphthquinolyl), and aromatic heterocyclic hydrocarbon groups (e.g., thienyl (a group derived from thiophene), furil (a group derived from furan), pyranyl (a group derived from pyrane), pyridyl (a group derived from pyridine), 9-oxoxanthenyl (a group derived from xanthone), and 9-oxothioxanthenyl (a group derived from thioxanthone)). As the aryl group, there can be used, besides the groups listed above, substituted aryl groups resulting from substitution of some hydrogen atoms of aryl groups with a hydroxyl group, a nitro group, a cyano group, a halogen atom, an alkoxy group having from 1 to 18 carbon atoms and/or an alkylthio groups having from 1 to 18 carbon atoms.

Among $R^3$ to $R^8$, the alkyl groups having from 1 to 8 (preferably 1 to 4) carbon atoms include alkyl groups having from 1 to 8 carbon atoms among the aforementioned alkyl groups. As the alkyl group, there can be used, besides the groups listed above, substituted alkyl groups resulting from substitution of some hydrogen atoms of alkyl groups with a hydroxyl group, a nitro group, a cyano group, a halogen atom, an aryl group having from 6 to 14 carbon atoms, an alkoxy group having from 1 to 18 carbon atoms and/or an alkylthio groups having from 1 to 8 carbon atoms.

Among $R^3$ to $R^8$, the aryl groups having from 6 to 12 carbon atoms include aryl groups having from 6 to 12 carbon atoms among the aforementioned aryl groups. As the aryl group, there can be used, besides the groups listed above, substituted aryl groups resulting from substitution of some hydrogen atoms of aryl groups with a hydroxyl group, a nitro group, a cyano group, a halogen atom, an alkoxy group having from 1 to 18 carbon atoms and/or an alkylthio groups having from 1 to 8 carbon atoms.

Examples of the alkoxy group represented by $-OR^3$ include methoxy, ethoxy, n-propoxy, iso-propoxy, n-butoxy, sec-butoxy, tert-butoxy, n-pentoxy, iso-pentoxy, neo-pentoxy, and 2-methylbutoxy. Examples of the amino group represented by $-NR^4R^5$ include methylamino, ethylamino, propylamino, dimethylamino, diethylamino, methylethylamino, dipropylamino, dipropylamino, and piperidino. Examples of the acyl group represented by $R^6CO-$ include acetyl, propanoyl, butanoyl, pivaloyl, and benzoyl. Examples of the acyloxy group represented by $R^7COO-$ include acetoxy, butanoyloxy, and benzoyloxy. Examples of the alkylthio group or the arylthio group represented by $-SR^8$ include methylthio, ethylthio, butylthio, hexylthio, cyclohexylthio, benzylthio, phenylthio, and 4-methylphenylthio. Examples of the halogen atom include a fluorine atom, a chlorine atom, a bromine atom, and an iodine atom.

If a substituent ($R^1$) or a substituent ($R^2$) is attached, the absorption wavelength of thioxanthone or anthracene, which is a base skeleton, can be shifted toward longer wavelengths. Even though thioxanthone and anthracene to which no substituent ($R^1$) or no substituent ($R^2$) is attached also absorb light of 350 nm or more, it is preferable that they have a substituent ($R^1$) and a substituent ($R^2$) attached thereto because making them have absorption also at longer wavelengths (400 nm or more) will lead to increase in efficiency of photodegradability.

A degree to shift (i.e., a shift value) varies depending upon the kinds of the substituent ($R^1$) and the substituent ($R^2$). Regarding the shift value, tables disclosed in "SPECTROMETRIC IDENTIFICATION OF ORGANIC COMPOUNDS Fifth Edition (written by R. M. Silverstein et al., p. 281, 1993, Tokyo Kagaku Dojin)" is informative.

From viewpoints of the aforementioned shift value, and the like, a hydroxyl group, alkoxy groups having from 1 to 4 carbon atoms, acyloxy groups having from 1 to 4 carbon atoms (an acetoxy group is particularly preferable), a nitro group, and a cyano group are preferable as the substituent ($R^1$).

From viewpoints of the aforementioned shift value, and on the like, alkoxy groups having from 1 to 4 carbon atoms, acyl groups having from 1 to 7 carbon atoms, a nitro group, and a cyano group are preferable as the substituent ($R^2$), and a butoxy group, an acetyl group, and a benzoyl group, are more preferable.

n is an integer of from 0 to 7, and from a viewpoint of photodegradability, it is preferably from 1 to 4, more preferably from 1 to 3, and particularly preferably 1 or 2.

m is an integer of from 0 to 9, and from a viewpoint of photodegradability, it is preferably from 1 to 4, more preferably from 1 to 3, and particularly preferably 1 or 2.

Although it is necessary only that the substituent ($R^1$) should be attached to a position other than the substituted site of a substituent represented by $CH_2-Y^+X^-$ among the 1- to 8-positions of a thioxanthone skeleton, it is preferable that the substituent ($R^1$) be attached to the 3-position or 7-position when the substituent represented by $CH_2-Y^+X^-$ is attached to the 2-position, it is preferable that the substituent ($R^1$) be attached to the 2-position when the substituent represented by $CH_2-Y^+X^-$ is attached to the 3-position, and it is preferable that the substituent ($R^1$) be attached to the 2-position or the 3-position or both when the substituent represented by $CH_2-Y^+X^-$ is attached to the 4-position.

When n is an integer of 2 or more, n $R^1$s may be either the same or different.

Although it is necessary only that the substituent ($R^2$) should be attached to a position other than the substituted site of the substituent represented by $CH_2-Y^+X^-$ among the 1- to 10-positions of an anthracene skeleton, it is preferable that the substituent ($R^2$) be attached to the 1-, 2-, 3-, 4- or 10-position, and it is more preferable, from a viewpoint of thermal stability, that it be attached to the 10-position (it is preferable that the substituent represented by $CH_2-Y^+X^-$ be attached to the 9-position when the substituent ($R^2$) is attached to the 10-position).

When m is an integer of 2 or more, m $R^2$s may be either the same or different.

The quaternary ammonio group ($Y^+$) leaves in the form of a corresponding amine with light irradiation, so that it functions as various reaction catalysts. On the other hand, since the quaternary ammonio group ($Y^+$) does not have basicity before light irradiation, the storage stability of a reactive composition does not deteriorate even if the group is contained in the reactive composition.

Examples of a quaternary ammonio group represented by general formula (5) include 1-azabicyclo[2.2.2]octan-1-yl (a group derived from quinuclidine, a group represented by chemical formula (12)), 3-hydroxy-1-azabicyclo[2.2.2]octan-1-yl (a group derived from 3-quinuclidinol, a group represented by chemical formula (13)), and 1,4-diazabicyclo[2.2.2]octan-1-yl (a group represented by chemical formula (14)).

[Chem. 4]

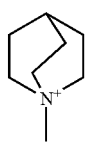
(12)

[Chem. 5]

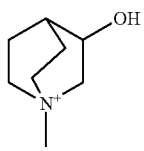
(13)

[Chem. 6]

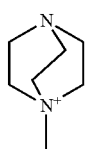
(14)

Examples of a quaternary ammonio group represented by general formula (6) include triethylammonio, tributylammonio, trioctylammonio, octyldimethylammonio, and dodecyloctylmethylammonio.

Among these ammonio groups, 1,8-diazabicyclo[5.4.0]-7-undecen-8-yl (a group represented by chemical formula (3)), 1,5-diazabicyclo[4.3.0]-5-nonen-5-yl (a group represented by chemical formula (4)), 1-azabicyclo[2.2.2]octan-1-yl (a group represented by chemical formula (12)), 3-hydroxy-1-azabicyclo[2.2.2]octan-1-yl (a group represented by chemical formula (13)), and 1,4-diazabicyclo[2.2.2]octan-1-yl (a group represented by chemical formula (14)) are preferable, and 1,8-diazabicyclo[5.4.0]-7-undecen-8-yl (a group represented by chemical formula (3)) and 1,5-diazabicyclo[5.4.0]-5-nonen-5-yl (a group represented by chemical formula (4)) are more preferable.

Although the substituent represented by $CH_2$—$Y^+X^-$ is only needed to be attached to any substitutable position among the 1- to 8-positions of a thioxanthone skeleton in the case of general formula (1), it preferably is attached to the 2-, 3- or 4-position and, from the viewpoint of thermal stability, it more preferably is attached to the 2- or 4-position.

Although the substituent represented by $CH_2$—$Y^+X^-$ is only needed to be attached to any substitutable position among the 1- to 10-positions of an anthracene skeleton in the case of general formula (2), it preferably is attached to the 1-, 2- or 9-position and, from the viewpoint of thermal stability, it more preferably is attached to the 9-position.

The counter anion ($X^-$) includes borate anions (e.g., tetraphenylborate, methyltriphenylborate, ethyl triphenylborate, propyltriphenylborate, and butyltriphenylborate), phenolate anions (e.g., phenolate, 4-tert-butylphenolate, 2,5-di-tert-butylphenolate, 4-nitrophenolate, 2,5-dinitrophenolate, and 2,4,6-trinitrophenolate) and carboxylate anions (e.g., a benzoate anion, a toluate anion, and a phenylglyoxylate anion). Among these, borate anions and carboxylate anions are preferable from the viewpoint of photodegradability, and a butyltriphenylborate anion, a tetraphenylborate anion, a benzoate anion, and a phenylglyoxylate anion are more preferable, and a tetraphenylborate anion and a phenylglyoxylate anion are particularly preferable from the viewpoint of photodegradability and thermal stability.

Among photobase generators represented by general formula (1), photobase generators represented by general formula (7), wherein $R^1$ is an alkoxy group having from 1 to 4 carbon atoms and $Y^+$ is a quaternary ammonio group represented by general formula (3) or (4), photobase generators represented by general formula (8), wherein $Y^+$ is a quaternary ammonio group represented by general formula (3) or (4), photobase generators represented by general formula (9), wherein $R^1$ is a hydroxyl group, an alkoxy group having from 1 to 4 carbon atoms or an acetoxy group, and $Y^+$ is a quaternary ammonio group represented by general formula (3) or (4), and photobase generators represented by general formula (10), wherein $Y^+$ is a quaternary ammonio group represented by general formula (3) or (4) are preferable.

[Chem. 7]

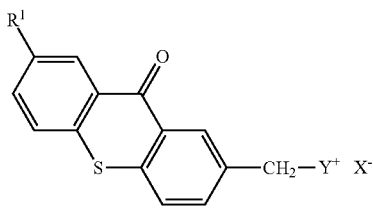
(7)

[Chem. 8]

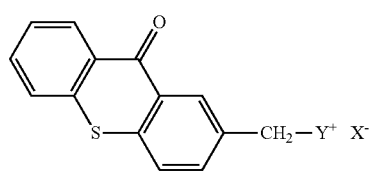
(8)

$X^-$ is a counter anion selected from among borate anions, phenolate anions, and carboxylate anions.

[Chem. 9]

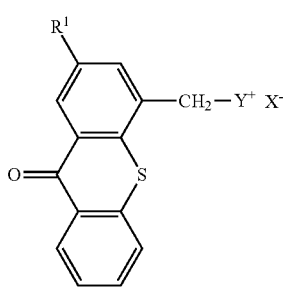
(9)

[Chem. 10]

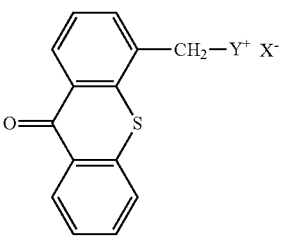
(10)

$X^-$ is a counter anion selected from among borate anions, phenolate anions, and carboxylate anions.

Among the photobase generators represented by general formula (2), photobase generators represented by general formula (11), wherein $R^2$ is an alkoxy group having from 1 to 4 carbon atoms, an acetyl group or a benzoyl group and $Y^+$ is a quaternary ammonio group represented by general formula (3) or (4) are preferable.

[Chem. 11]

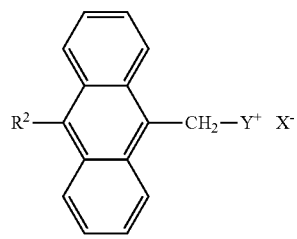

(11)

$X^-$ is a counter anion selected from among borate anions, phenolate anions, and carboxylate anions.

Preferable examples of the photobase generators represented by general formula (1) include compounds represented by the following chemical formulae.

[Chem. 12]

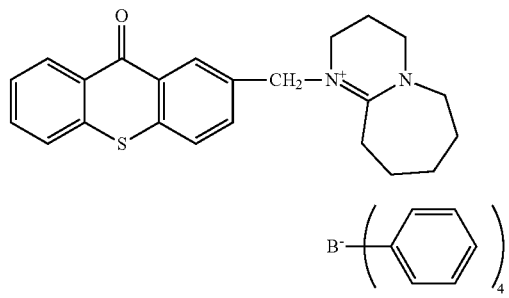

(1-1)

[Chem. 13]

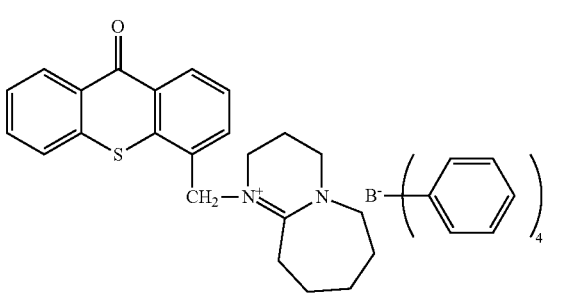

(1-2)

[Chem. 14]

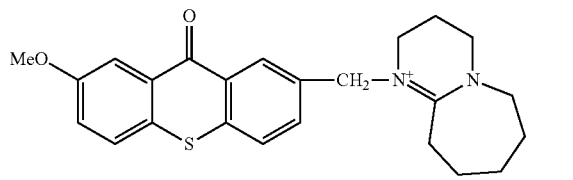

(1-3)

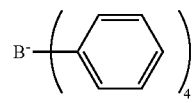

[Chem. 15]

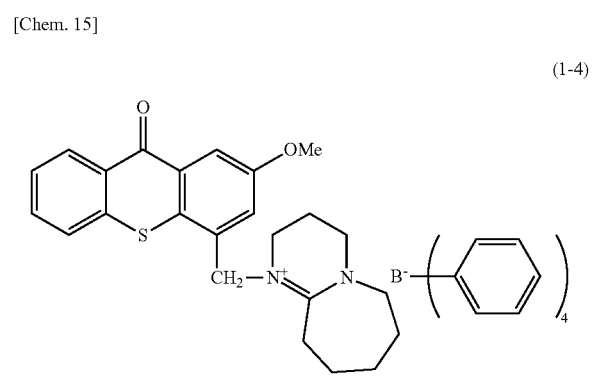

(1-4)

[Chem. 16]

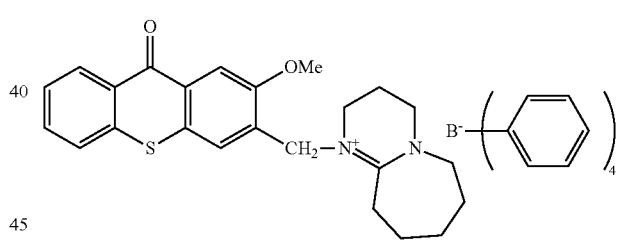

(1-5)

[Chem. 17]

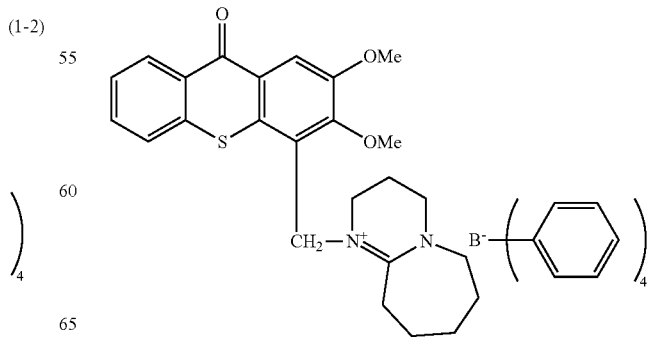

(1-6)

-continued
[Chem. 18]
(1-7)
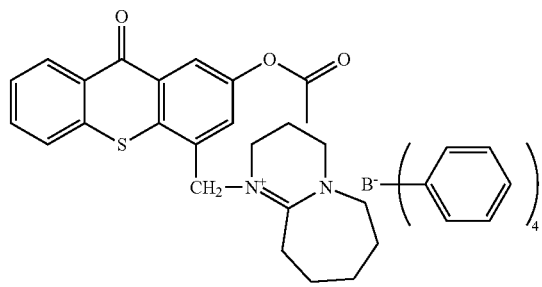
[Chem. 19]
(1-8)
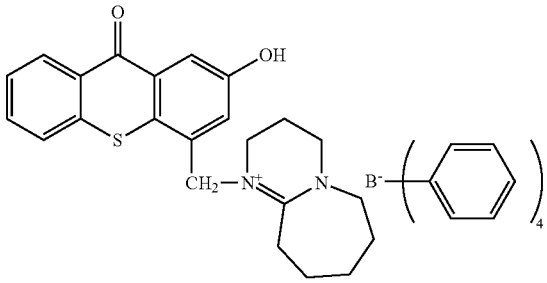
[Chem. 20]
(1-9)
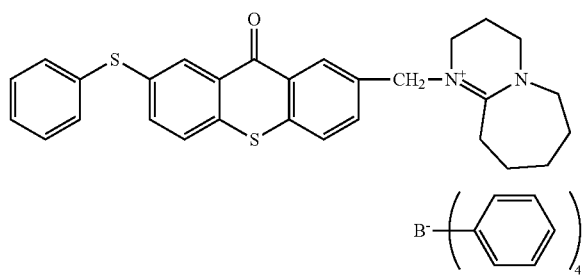
[Chem. 21]
(1-10)
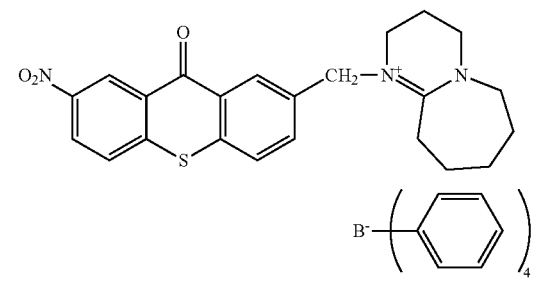
-continued
[Chem. 22]
(1-11)
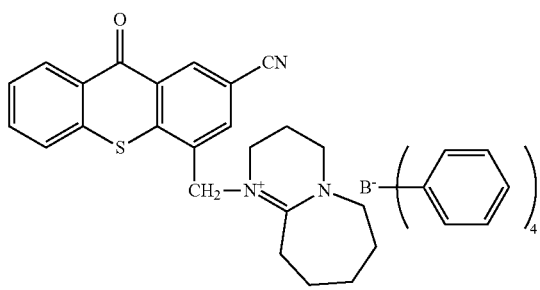
[Chem. 23]
(1-12)
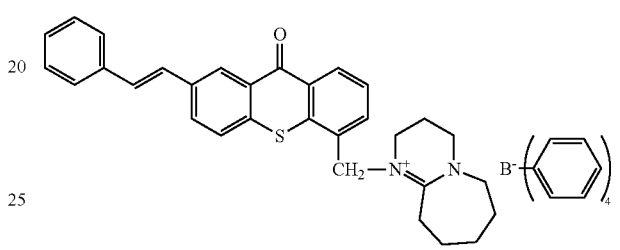
The following are preferably provided as examples of the photobase generators represented by general formula (2).
[Chem. 24]
(2-1)
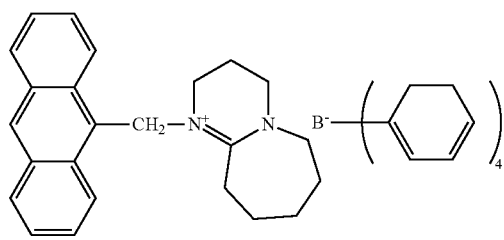
[Chem. 25]
(2-2)
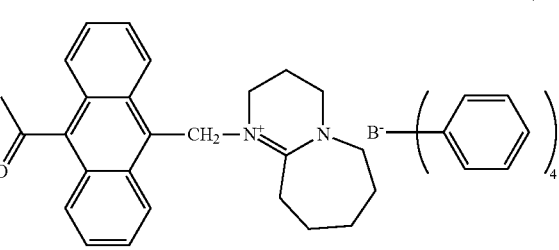
[Chem. 26]
(2-3)

[Chem. 27]
(2-4)
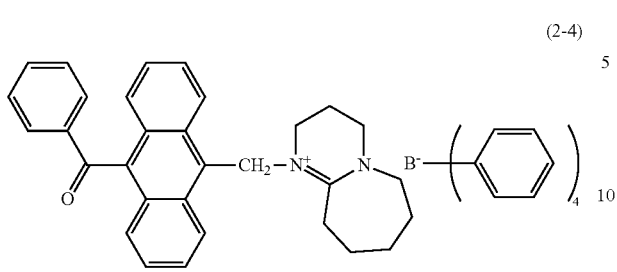
[Chem. 28]
(2-5)
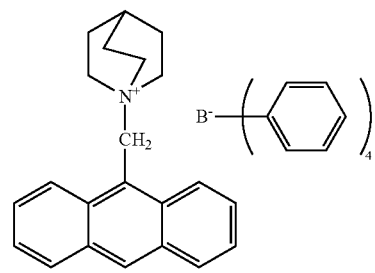
[Chem. 29]
(2-6)
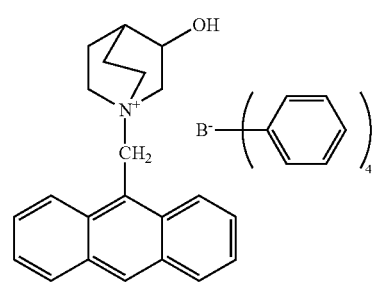
[Chem. 30]
(2-7)
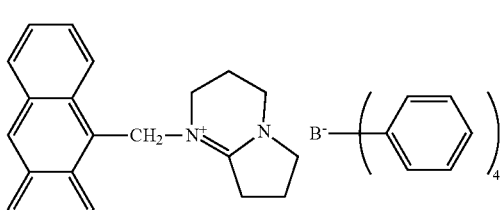
[Chem. 31]
(2-8)
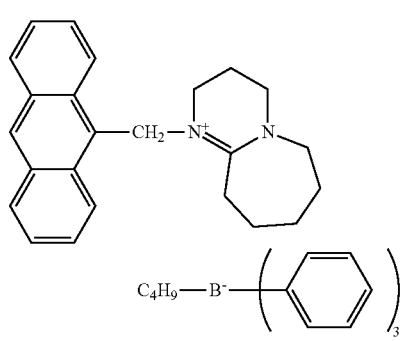
[Chem. 32]
(2-9)
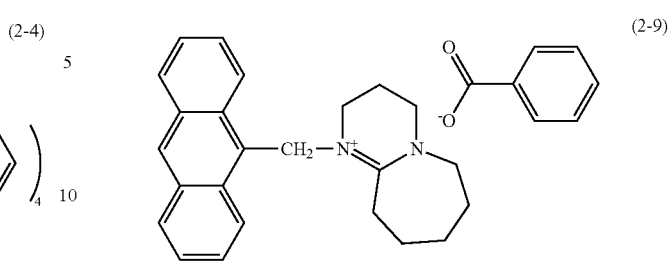
[Chem. 33]
(2-10)
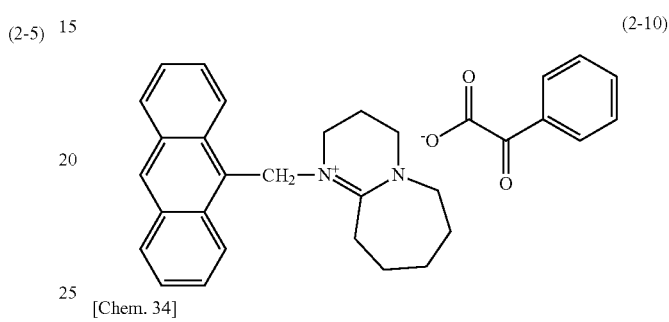
[Chem. 34]
(2-11)
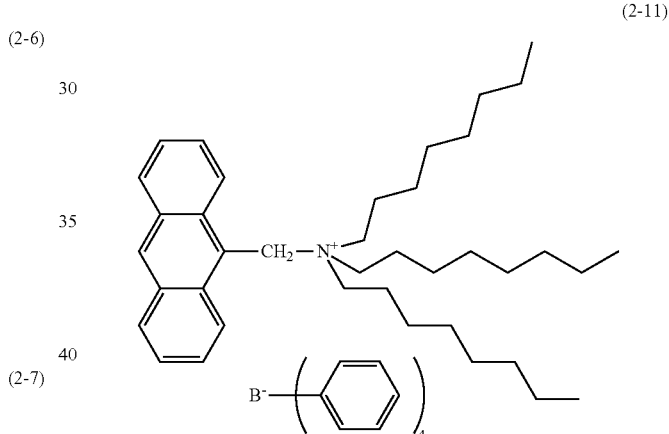
[Chem. 35]
(2-12)
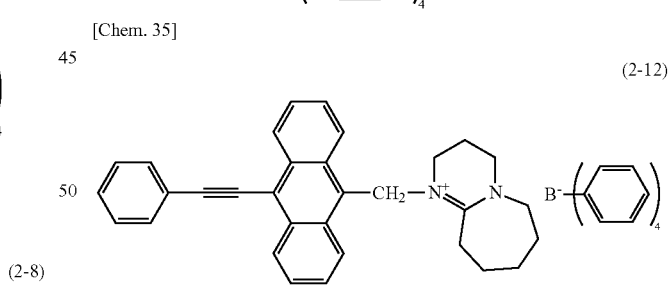
[Chem. 36]
(2-13)
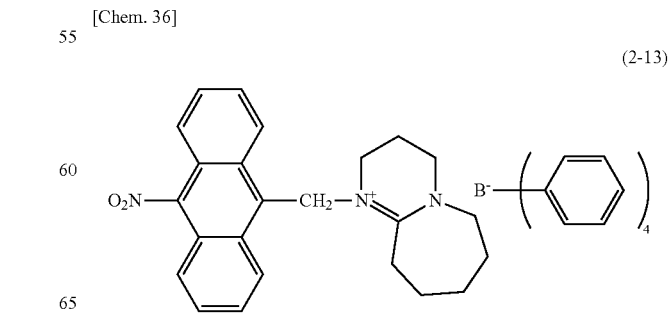

-continued

[Chem. 37]

(2-14)

The photobase generator of the present invention can be produced by a known method, and for example, a desired photobase generator can be obtained by making a thioxanthone or anthracene corresponding to the desired photobase generator which has a methyl group having a substituent ($R^1$ or $R^2$) and a leaving group (Z) react with an amine corresponding to a quaternary ammonio group ($Y^+$) in an organic solvent to obtain an intermediate which has $Z^-$ as a counter anion, and then anion-exchanging with $M^+X^-$ as illustrated in the following chemical reaction formulae.

[Chem. 38]

<A photobase generator represented by general formula (1)>

[Chem. 39]

<A Photobase Generator Represented by General Formula (2)>

In the chemical reaction formulae shown above, $R^1$, $R^2$, $Y^+$, $X^-$, n and m are the same as those in general formulae (1) and (2), Z is a leaving group, $Z^-$ is an anion generated through elimination, and $M^+$ is a metal cation.

Examples of the amine include an amine represented by chemical formula (15) {1,8-diazabicyclo[5.4.0]-undecene-7 (DBU; "DBU" is a registered trademark of San-Apro Ltd.)}, an amine represented by chemical formula (16) {1,5-diazabicyclo[4.3.0]-nonene-5 (DBN)}, amines represented by chemical formula (17) {each sign is the same as that of chemical formula (5); e.g., 1-azabicyclo[2.2.2]octane, 3-hydroxy-1-azabicyclo[2.2.2]octane, and 1,4-diazabicyclo[2.2.2]octane}, and amines represented by chemical formula (18) {each sign is the same as that of chemical formula (6); e.g., trialkylamines (e.g., triethylamine, tributylamine, trioctylamine, octyldimethylamine, and dodecyloctylmethylamine), trialkenylamines (e.g., triallylamine), and triarylamines (e.g., triphenylamine, tri-p-tolylamine, and diphenyl-p-tolylamine)}.

[Chem. 40]

(15)

(16)

(17)

(18)

Examples of the leaving group (Z) include halogen atoms (e.g., a chlorine atom and a bromine atom), sulfonyloxy groups (e.g., trifluoromethylsulfonyloxy, 4-methylphenylslufonyloxy, and methylsulfonyloxy), and acyloxy (e.g., acetoxy and trifluoromethylcarbonyloxy). Among these, a halogen atom and a sulfonyloxy group are preferable from the viewpoint of ease of production.

The organic solvent includes cyclic ethers (e.g., tetrahydrofuran and dioxane), chlorinated solvents (e.g., chloroform and dichloromethane), alcohols (e.g., methanol, ethanol, and isopropylalcohol), ketones (e.g., acetone, methylethylketone, and methylisobutylketone), nitriles (e.g., acetonitrile), and polar organic solvents (e.g., dimethylsulfoxide, dimethylformamide, and N-methylpyrrolidone). These solvents may be used singly and two or more of them also may be used together.

The reaction temperature (° C.) of the thioxanthone or anthracene having a substituent ($R^1$ or $R^2$) and a methyl group having an leaving group (Z) with an amine corresponding to a quaternary ammonio group ($Y^+$) is preferably from −10 to 100 and more preferably from 0 to 80.

It is preferable to dissolve the thioxanthone or anthracene having a substituent ($R^1$ or $R^2$) and a methyl group having a leaving group (Z) in the organic solvent and then add the amine thereto. Regarding the method of adding the amine, it may be dropped and also may be dropped after being diluted with an organic solvent.

The $X^-$ of $M^+X^-$ includes borate anions (e.g., tetraphenylborate, methyltriphenylborate, ethyl triphenylborate, propyltriphenylborate, and butyltriphenylborate), phenolate anions (e.g., phenolate, 4-tert-butylphenolate, 2,5-di-tert-butylphenolate, 4-nitrophenolate, 2,5-dinitrophenolate, and 2,4,6-trinitrophenolate), and carboxylate anions (benzoate anion, toluate anion, and phenylglyoxylate anion).

The $M^+$ of $M^+X^-$ includes alkali metal ions (e.g., sodium ion and potassium ion) and silver ion.

The anion exchange is performed by transforming a salt ($M^+X^-$) into an aqueous solution and mixing this with an organic solvent solution containing an intermediate. A salt ($M^+Z^-$) generated by the anion exchange can be separated and removed easily from the organic solvent phase because it precipitates (silver salt) or dissolves in the aqueous phase.

After obtaining an intermediate, anion exchange may be performed subsequently or, in the alternative, anion exchange may be performed after isolating and purifying the intermediate and then dissolving it in an organic solvent again.

The photobase generator to be obtained in the above-mentioned way may be refined after being separate from the organic solvent. The separation from the organic solvent can be performed by depositing the photobase generator by adding a poor solvent to the organic solvent solution containing the photobase generator directly (or after the condensation thereof). The poor solvent to be used here includes chain ethers (e.g., diethyl ether and dipropyl ether), esters (e.g., ethyl acetate and butyl acetate), aliphatic hydrocarbons (e.g., hexane and cyclohexane), and aromatic hydrocarbons (e.g., toluene and xylene).

When the photobase generator is oily matter, the photobase generator of the present invention can be obtained by separating the deposited oily matter from an organic solvent solution and evaporating the organic solvent contained in the oily matter. On the other hand, when the photobase generator is a solid, the photobase generator of the present invention can be obtained by separating a deposited solid from an organic solvent solution and evaporating the organic solvent contained in the solid.

The refining can be performed by recrystallization (a method of using the solubility difference caused by cooling, a method of forming deposition by adding a poor solvent, and combined use of the methods). When the photobase generator is oily matter (when it does not crystallize), it can be refined by a method of washing the oily matter with water or a poor solvent.

A thioxanthone or anthracene having a substituent ($R^1$ or $R^2$) corresponding to a desired photobase generator and a methyl group having a leaving group (Z) can be produced by a known method.

The thioxanthone or anthracene having a substituent ($R^1$ or $R^2$) corresponding to a desired photobase generator and a methyl group having a leaving group (Z) can be produced either by producing a methylthioxanthone or methylanthracene having a substituent ($R^1$ or $R^2$) corresponding to a desired photobase generator and then introducing an leaving group (Z) into the methyl group or by formylating a thioxanthone or anthracene having a substituent ($R^1$ or $R^2$) corresponding to a desired photobase generator, reducing it, and then introducing an leaving group (z). Hereafter, these methods are explained briefly.

A methylthioxanthone having a substituent ($R^1$) corresponding to a desired photobase generator can be produced by, for example, (1) a method in which thiosalicylic acid or dithiosalicylic acid and an aromatic compound (e.g., toluene) are made react together in sulfuric acid (J. Am. Chem. Soc. (74) 4296 (1952); the contents disclosed in this document are incorporated herein by reference) or (2) a method in which o-halogenated benzoic acid and thiophenol or thiobenzoic acid and an aryl halide are made undergo a coupling reaction in the presence of a metallic catalyst and then a ring is formed by a dehydration reaction ((Arch. Pharm. (Weinheim) 326, 451 (1993), Chem. Pharm. Bull. 35 (6) 2545 (1987); the contents disclosed in the documents are incorporated herein by reference) (see the following chemical formulae).

[Chem. 41]

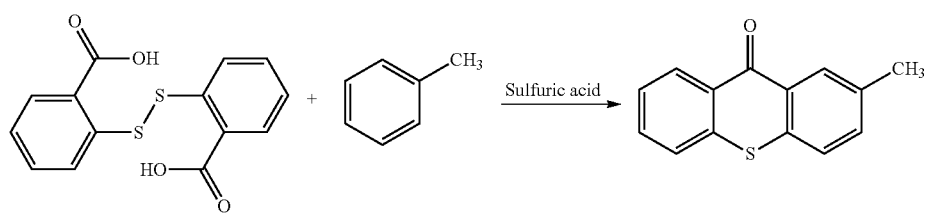

[Chem. 42]

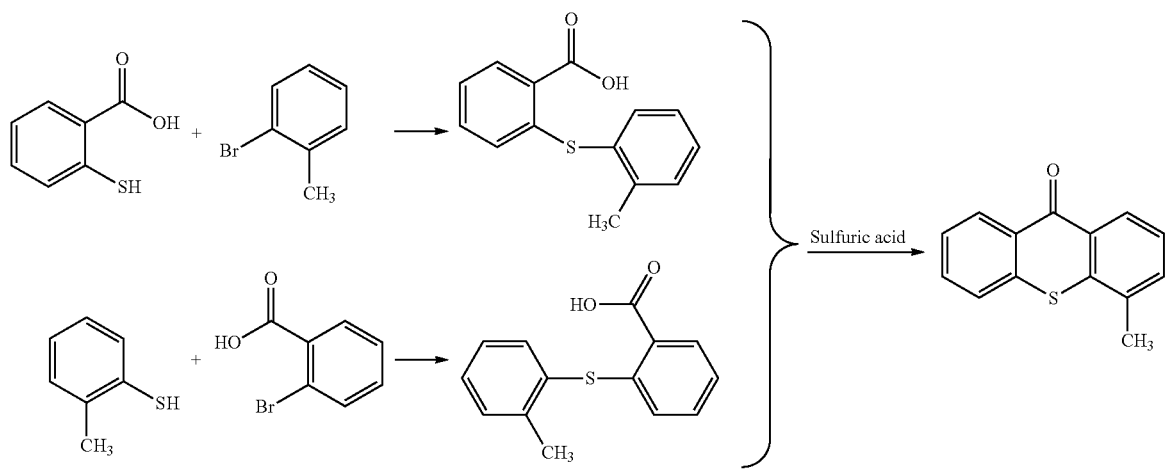

Besides the above, in order to introduce a substituent ($R^1$) into a thioxanthone skeleton, Indian Journal of Chemistry (20) 50 (1981) is informative when introducing a nitro group, Chemische Berichte (49) 2487 (1916) is informative when introducing an alkoxy group or a halogen atom, and Journal of the Chemical Society (99) 2047 (1911) is informative when introducing a hydroxyl group (the contents disclosed in these documents are incorporated herein by reference). When introducing an amino group, a product is obtained by reducing a nitro group and it may, for example, be N-alkylated or N-arylated with an alkylating agent or an arylating agent.

An anthracene having a substituent ($R^2$) corresponding to a desired photobase generator can be produced by, for example, a method in which an alkoxyanthracene is obtained by making an alkyl halide react under basicity by using anthrone as a starting substance when $R^2$ is an alkoxy group (J. Photochem. Photobio. A; Chem (159) 173 (2003); the contents disclosed in this document are incorporated herein by reference) (see the following chemical formula).

[Chem. 43]

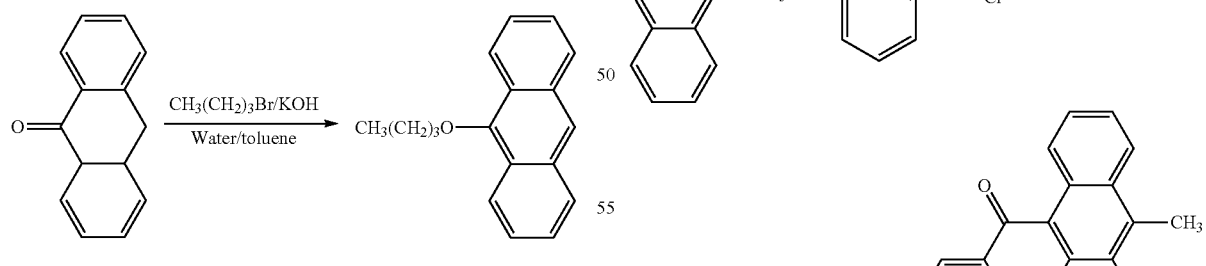

A methylanthracene having a substituent ($R^2$) corresponding to a desired photobase generator can be produced by, for example, (1) a method in which methylanthracene and an acid anhydride are made react together in the presence of a strong acid (methanesulfonic acid) when $R^2$ is an acyl group or (2) a method in which a Friedel-Crafts reaction in the presence of a Lewis acid (Jikken Kagaku Koza, 4th Edition, Vol. 21, p. 275, edited by The Chemical Society of Japan) (see the following chemical formula).

[Chem. 44]

Besides the above, in order to introduce a substituent ($R^2$) into an anthracene skeleton, Tetrahedron: Asynmetry, 18(8) 1003 (2007) is informative when introducing a nitro group, Organic Letters, 8(6) 1189 (2006) is informative when introducing a cyano group, Journal of Organometallic Chemistry, 691, p. 1389 (2006) is informative when introducing an alkenyl group and an alkenyl group, Bull. Chem. Soc. Jpn., (53) 1385 (1980) is informative when introducing an alkylthio group and an arylthio group, The Journal of Organic Chemistry (65) 3005 (2000) is informative when introducing a halogen atom, Journal of the American Chemical Society (69) 1038 (1941) is informative when introducing an acetoxy group, and Organic Synthesis, Coll. Vol. 5, 918 (1973) is informative when introducing a hydroxyl group (the contents disclosed in these documents are incorporated herein by reference). When introducing an amino group, a product is obtained by reducing a nitro group and it may, for example, be N-alkylated or N-arylated with an alkylating agent or an arylating agent.

Regarding a thioxanthone or anthracene having a substituent ($R^1$ or $R^2$) corresponding to a desired photobase generator and a methyl group having a leaving group (Z), a thioxanthone or anthracene having a methyl group having a leaving group (Z) (e.g., bromomethylthioxanthone and bromomethylanthracene) can be obtained by halogenating (preferably, brominating) a methyl group of methylthioxanthone or methylanthracene.

Although the halogenation (preferably, bromination) can be performed by various methods, a method in which halogen (preferably, bromine) is used or a method in which N-bromosuccinimide is used together with a radical generator is simple and convenient and therefore is preferable (Jikken Kagaku Koza, 4th Edition, Vol. 19, p. 422, edited by The Chemical Society of Japan).

When methylthioxanthone or methylanthracene is not available, a thioxanthone or anthracene having a substituent ($R^1$ or $R^2$) corresponding to a desired photobase generator and a methyl group having a leaving group (Z) can be produced by the following method. Specifically, a thioxanthone or anthracene having a substituent ($R^1$ or $R^2$) corresponding to a desired photobase generator and a methyl group having a leaving group (z) can be obtained by obtaining an aldehyde from thioxanthone or anthracene by formylation using (1) Vilsmeier method (Jikken Kagaku Koza, 4th Edition, Vol. 21, p. 106, edited by The Chemical Society of Japan), then reducing it into an alcohol with a reducing agent (e.g., sodium borohydride) (Jikken Kagaku Koza, 4th Edition, Vol. 20, p. 1, edited by The Chemical Society of Japan), and further converting the alcohol into halogen by using a halogenating agent (Jikken Kagaku Koza, 4th Edition, Vol. 19, p. 422, edited by The Chemical Society of Japan) or making the alcohol react with an acid corresponding to the leaving group (Z), its acid halide, or its acid anhydride (the following chemical formula is an example about an alkoxyanthracene, wherein TsOH denotes p-toluenesulfonic acid and Ts denotes a group represented by p-$CH_3C_6H_4SO_2$—).

[Chem. 45]

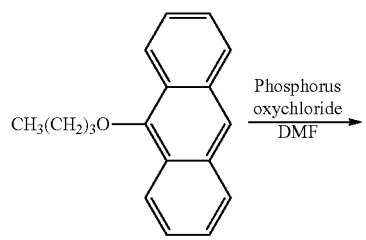

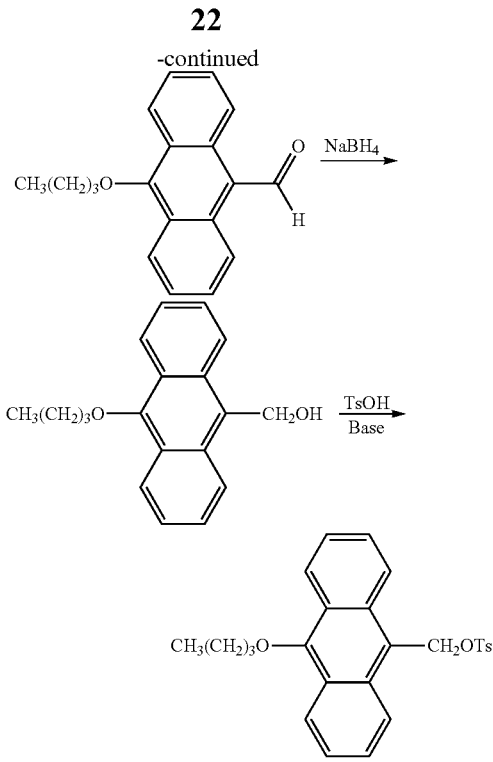

The photobase generator of the present invention can be applied, for example, as a latent base catalyst (i.e., a catalyst that has no catalysis before light is applied but develops an action of a base catalyst through light irradiation); for example, it can be used as a curing catalyst for a curable resin composition and, in particular, it is suitable as a curing catalyst for a curable resin which will be cured when light of from 350 to 500 nm (preferably from 400 to 500 nm) is applied thereto. For example, a curable resin composition containing a basic resin to be cured with a base, the photobase generator of the present invention and, if necessary, a solvent and/or an additive can be constituted easily. Such a curable resin composition is excellent in storage stability and also in curability because it contains the photobase generator of the present invention. That is, it is possible to obtain a cured resin (a cured product) by promoting a curing reaction by generating a base by irradiating a curable resin composition containing the photobase generator of the present invention with light having a wavelength of from 350 to 500 nm (preferably, from 400 to 500 nm). Therefore, a production method of such a cured resin (a cured product) preferably includes a step of generating a base by irradiating the photobase generator of the present invention with light having a wavelength of from 350 to 500 nm (preferably, from 400 to 500 nm). In a curing reaction, heat curing may be used together, if necessary.

The basic resin to be cured with a base is not particularly restricted if it is a curable resin which is capable of curing by a base, and examples thereof include curable urethane resins {e.g., resins comprising a (poly)isocyanate and a curing agent (e.g., a polyol and a thiol)}, curable epoxy resins {e.g., a resin comprising a (poly)epoxide and a curing agent (e.g., an acid anhydride, a carboxylic acid, a (poly)epoxide, a thiol, and the like), and a resin composed of epichlorohydrin and a carboxylic acid}, curable acrylate resins an acrylic monomer and/or an acrylic oligomer, and a curing agent (e.g., a thiol, a malonic ester, and acetylacetonato)}, polysiloxane (this cures to become crosslinked polysiloxane), and resins disclosed in patent document 3.

Since the photobase generator of the present invention is sensitive also to light having a wavelength of 400 nm or more, there can be used not only high-pressure mercury-vapor lamps, which are generally used, but also ultrahigh pressure mercury lamps, metal halide lamps, and high power metal halide lamps (Recent Advances in UV/EB Radiation Curing Technology, edited by RadTech Japan, published by CMC Publishing CO., LTD., p. 138, 2006).

EXAMPLES

Hereafter, % means % by weight % unless otherwise stated.

Example 1

Synthesis of 8-(9-oxo-9H-thioxanthen-2-yl)methyl-1,8-diazabicyclo[5.4.0]-7-undecenium tetraphenylborate {a photobase generator represented by chemical formula (1-1)}

(1) Synthesis of methylthioxanthone (intermediate 10)

Into an Erlenmeyer flask was charged 139 g of sulfuric acid, and 10 g of dithiosalicylic acid (Wako Pure Chemical Industries, Ltd.) was added thereto. After stirring at room temperature (about 25° C.) for 1 hour and then cooling in an ice bath, a cooled solution was obtained. Subsequently, 25 g of toluene was dropped slowly while the temperature of the cooled solution was kept at 20° C. or lower, and then the temperature was returned to room temperature (about 25° C.) and stirring was continued for additional 2 hours, so that a reaction liquid was obtained. While 815 g of water contained in a beaker was being stirred, the reaction liquid was added thereto slowly, and then a precipitated yellow solid was collected by filtration. The yellow solid was dissolved in 260 g of dichloromethane and 150 g of water was added. Moreover, 6.7 g of 24% aqueous KOH solution was added to make the aqueous layer alkaline, followed by stirring for 1 hour. Then the aqueous layer was removed by a separatory operation and the organic layer was washed with 130 g of water three times. Subsequently, the organic layer was dried over anhydrous sodium sulfate and then the solvent (dichloromethane) was distilled away, so that 8.7 g of intermediate (10) (yellow solid) was obtained. As a result of an analysis by $^1$H-NMR {300 MHz, DMSO-d6, δ (ppm): 8.4 (d, 1H), 8.2 (s, 1H), 7.8-7.7 (m, 2H), 7.7-7.5 (m, 3H), 2.4 (s, 3H)}, it was confirmed that intermediate (10) was a mixture (molar ratio 2:1) of 2-methylthioxanthone and 3-methylthioxanthone.

(2) Synthesis of 2-bromomethylthioxanthone (intermediate 11)

In 120 ml of cyclohexane was dissolved 2.1 g of intermediate (10) (a methylthioxanthone mixture), and 8.3 g of N-bromosuccinimide (Wako Pure Chemical Industries, Ltd.) and 0.1 g of benzoyl peroxide (Wako Pure Chemical Industries, Ltd.) were added thereto. After a reaction was performed under reflux for 4 hours (3-methylthioxanthone failed to react), the solvent (cyclohexane) was distilled away, and 50 ml of chloroform was added thereto to dissolve the residue again, so that a chloroform solution was obtained. The chloroform solution was washed with 30 g of water three times and the aqueous layer was removed by a separatory operation. Then, the solvent (chloroform) was distilled away, so that 1.7 g of a brown solid was obtained.

By recrystallizing this with ethyl acetate, 1.5 g of intermediate (11) (yellow solid) was obtained. As a result of an analysis by $^1$H-NMR {300 MHz, DMSO-d6, δ (ppm): 8.6 (s, 2H), 7.8-7.5 (m, 5H), 4.6 (s, 2H)}, it was confirmed that intermediate (11) was 2-bromomethylthioxanthone.

(3) Synthesis of 8-(9-oxo-9H-thioxanthen-2-yl)methyl-1,8-diazabicyclo[5.4.0]-7-undecenium bromide (intermediate 12)

In 85 g of dicyclomethane was dissolved 1.0 g of intermediate (11) (2-bromomethylthioxanthone), and 0.5 g of 1,8-diazabicyclo[5.4.0]-7-undecene (DBU, San-Apro Ltd.) was dropped thereto (heat was generated after the dropping). By stirring them under room temperature (about 25° C.) for 1 hour and distilling dichloromethane away, 2.2 g of a white solid was obtained. This white solid was dissolved in tetrahydrofuran/dichloromethane and recrystallization was performed, so that 1.2 g of intermediate (12) (white solid) was obtained. As a result of an analysis by $^1$H-NMR {300 MHz, CDCl$_3$, δ (ppm): 8.6 (d, 1H), 8.3 (d, 1H), 7.8 (d, 1H), 7.8-7.6 (m, 3H), 7.5 (t, 1H), 5.1 (s, 2H), 3.9-3.8 (m, 6H), 3.0 (m, 2H), 2.4-2.2 (m, 2H), 2.0-1.7 (m, 6H)}, it was confirmed that intermediate (12) was 8-(9-oxo-9H-thioxanthen-2-yl)methyl-1,8-diazabicyclo[5.4.0]-7-undecenium bromide.

(4) Synthesis of 8-(9-oxo-9H-thioxanthen-2-yl)methyl-1,8-diazabicyclo[5.4.0]-7-undecenium tetraphenylborate To an aqueous solution prepared by dissolving 0.8 g of sodium tetraphenylborate (Nacalai Tesque, Inc.) in 17 g of water was dropped slowly 1.0 g of intermediate (12) (8-(9-oxo-9H-thioxanthen-2-yl)methyl-1,8-diazabicyclo[5.4.0]-7-undecenium bromide) dissolved beforehand in 50 g of chloroform. Stirring was then continued at room temperature (about 25° C.) for 1 hour, the aqueous layer was removed by a separatory operation, and the organic layer was washed with 30 g of water three times. The organic layer was condensed with an evaporator, and a yellow solid was obtained. This yellow solid was recrystallized from acetonitrile/ether, so that 1.3 g of a photobase generator (1-1) of the present invention (slightly yellow powder) was obtained. As a result of an analysis by $^1$H-NMR {300 MHz, DMSO-d6, δ (ppm): 8.5 (d, 1H), 8.4 (s, 1H), 8.0-7.6 (m, 5H), 5.1 (s, 2H), 3.8-3.7 (m, 2H), 3.7-3.5 (m, 4H), 3.0-2.9 (m, 2H), 2.1-2.0 (m, 2H), 1.8-1.5 (m, 6H)}, it was confirmed that this slightly yellow powder was 8-(9-oxo-9H-thioxanthen-2-yl)methyl-1,8-diazabicyclo[5.4.0]-7-undecenium tetraphenylborate.

Example 2

Synthesis of 8-(10-butoxy-9-anthryl)methyl-1,8-diazabicyclo[5.4.0]-7-undecenium tetraphenylborate {a photobase generator represented by chemical formula (2-2)}

(1) Synthesis of 9-butoxyanthracene (intermediate 20)

A mixed solution was prepared by adding 10.9 g of anthrone (Tokyo Chemical Industry Co., Ltd.), 23.6 g of toluene, 11.6 g of n-butyl bromide (Tokyo Chemical Industry Co., Ltd.), and 1.1 g of tetrabutylammonium bromide (Wako Pure Chemical Industries, Ltd.) to a four-necked, 100-mL flask. To this was added 13.2 g of 48% aqueous potassium hydroxide solution, followed by heating. After a reaction was performed under reflux for 5 hours, the reaction liquid was cooled to room temperature (about 25° C.) and was separated into an organic layer and an aqueous layer with a separatory funnel. The aqueous layer was extracted twice with 10 g of toluene, which were then combined with the organic layer. Subsequently, the combined organic layer was washed with 15 g of water three times, the organic layer was then dried over anhydrous sodium sulfate, and the organic solvent was distilled away with an evaporator, so that a pale yellow solid was obtained. Then 9.6 g of the pale yellow solid was subjected to a recrystallization operation with 30 g of isopropyl alcohol, so that 5.0 g of intermediate (20) (pale yellow solid) was obtained. As a result of an analysis by $^1$H-NMR {300 MHz, DMSO-d6, δ (ppm): 8.4-8.3 (m, 2H), 8.2 (s, 1H), 8.0 (m, 2H), 7.5 (m, 4H), 4.2 (t, 2H), 2.1 (m, 2H), 1.7 (m, 2H), 1.1 (t, 3H)}, it was confirmed that intermediate (20) was 9-butoxyanthracene.

(2) Synthesis of 9-butoxyanthracene-10-carbaldehyde (intermediate 21)

In a 50-ml eggplant flask, to a solution prepared by dissolving 1.1 g of intermediate (20) (9-butoxyanthracene) in 10 mL of N,N-dimethylformamide was dropped 10 ml of phosphorus oxychloride (some generation of heat was observed), and the temperature was raised by using an oil bath. A reaction was performed at 60° C. for 5 hours, and then a reaction liquid was cooled to room temperature (about 25° C.), so that the reaction liquid was obtained. While stirring 50 ml of ice water contained in a 100-ml beaker, the reaction liquid was added (a precipitate appeared immediately) and stirring was continued for 30 minutes. Then 50 ml of ethyl acetate was added and stirred for additional 15 minutes, followed by separation into an aqueous layer and an organic layer with a separatory funnel. The aqueous layer was extracted three times with 20 ml of ethyl acetate, which were combined with the organic layer. The combined organic layer was dried over anhydrous sodium sulfate and then the organic solvent was distilled away with an evaporator, so that 1.0 g of intermediate (21) (brown solid) was obtained. As a result of an analysis by $^1$H-NMR {300 MHz, DMSO-d6, δ (ppm): 11.5 (s, 1H), 9.0 (d, 2H), 8.4 (d, 2H), 7.7 (t, 2H), 7.6 (t, 2H), 4.2 (t, 2H), 2.1 (m, 2H), 1.7 (m, 2H), 1.1 (t, 3H)}, it was confirmed that intermediate (21) was 9-butoxyanthracene-10-carbaldehyde.

(3) Synthesis of 9-butoxy-10-hydroxymethylanthracene (intermediate 22)

A 100-ml eggplant flask was charged with 1.0 g of intermediate (21) (9-butoxyanthracen-10-carbaldehyde), which was then dissolved by adding 7.5 ml of tetrahydrofuran. There was added 0.04 g of sodium borohydride (Wako Pure Chemical Industries, Ltd.), and 7.5 ml of methanol was further added (at this time, bubbles were formed). Stirring was continued at room temperature (about 25° C.) for 6 hours, so that a reaction liquid was obtained. While stirring 50 g of water contained in a 100-ml beaker, the reaction liquid was charged slowly, and 40 g of chloroform was added thereto. After stirring for additional 10 minutes, the organic layer and the aqueous layer were separated with a separatory funnel. The aqueous layer was extracted twice with 20 g of chloroform, which were combined with the organic layer. The combined organic layer was dried over anhydrous sodium sulfate and then the organic solvent was distilled away with an evaporator, so that orange oil was obtained. By subjecting the orange oil to a recrystallization operation by using hexane, 0.6 g of intermediate (22) (yellow crystal) was obtained. As a result of an analysis by $^1$H-NMR {300 MHz, DMSO-d6, δ (ppm): 8.5 (t, 2H), 8.3 (t, 2H), 7.6-7.5 (m, 4H), 5.4 (d, 2H), 5.2 (t, 1H), 4.1 (t, 2H), 2.0 (m, 2H), 1.7 (m, 2H), 1.0 (t, 3H)}, it was confirmed that intermediate (22) was 9-butoxy-10-hydroxymethylanthracene.

(4) Synthesis of 8-(10-butoxy-9-anthryl)methyl-1,8-diazabicyclo[5.4.0]-7-undecenium tetraphenylborate A four-necked, 200-ml flask was charged with 4.2 g of intermediate (22) (9-butoxy-10-hydroxymethylanthracene), which was then dissolved by adding 40 ml of tetrahydrofuran. There was added a solution composed of 5.0 g of p-toluenesulfonyl chloride (Nacalai Tesque, Inc.) and 10 ml of tetrahydrofuran, and then 8.0 g of 1,8-diazabicyclo[5.4.0]-7-undecene (DBU, San-Apro Ltd.) was dropped (a solid started to precipitate slowly). Then a reaction was performed at 60° C. for 6 hours, followed by cooling to room temperature (about 25° C.), and 50 g of dichloromethane and 50 g of water were added thereto and stirred. Thus, the precipitated solid was dissolved and an organic layer and an aqueous layer were separated. This was separated by a separatory operation and the organic layer was washed further with 50 g of water twice. An aqueous solution composed of 3.4 g of sodium tetraphenylborate and 25 g of water was added to the organic layer, stirred vigorously for 1 hour, and then left at rest. The aqueous layer was then removed by a separatory operation. The organic layer was washed with 20 g of water three times and was dried over anhydrous sodium sulfate, and the solvent was distilled away, so that a yellow-brown solid was obtained. This yellow-brown solid was recrystallized from acetonitrile/ethanol, so that 10.8 g of a photobase generator (2-2) of the present invention (yellow crystal) was obtained. As a result of an analysis by $^1$H-NMR {300 MHz, DMSO-d6, δ (ppm): 8.4 (d, 2H), 8.3 (d, 2H), 7.8-7.6 (m, 4H), 7.3-7.1 (m, 8H), 7.0-6.8 (m, 8H), 6.8-6.7 (m, 4H), 5.8 (s, 2H), 4.2 (t, 2H), 3.8-3.7 (m, 2H), 3.5-3.3 (m, 6H), 2.8-2.7 (m, 2H), 2.0 (m, 2H), 1.9-1.6 (m, 10H), 1.0 (t, 3H)}, it was confirmed that this yellow crystal was 8-(10-butoxy-9-anthryl)methyl-1,8-diazabicyclo[5.4.0]-7-undecenium tetraphenylborate Example 3

Synthesis of 1-(9-anthryl)methyl-1-azabicyclo[2.2.2]octanium tetraphenylborate {a photobase generator represented by chemical formula (2-5)}

In chloroform in a 50-ml eggplant flask was dissolved 2.0 g of 9-chloromethylanthracene (Aldrich), and 1.0 g of 1-azabicyclo[2.2.2]octane (Aldrich) was added thereto little by little (after the addition, some generation of heat was observed). Stirring was continued at room temperature (about 25° C.) for 1 hour, so that a reaction liquid was obtained. The reaction liquid was dropped slowly into an aqueous solution composed of 4.0 g of sodium tetraphenylborate and 40 g of water contained in a 100-ml eggplant flask and further stirred at room temperature (about 25° C.) for 1 hour. Then the aqueous layer was removed by a separatory operation and the organic layer was washed with water three times. The organic layer was condensed with an evaporator, so that 5.4 g of a white solid was obtained. This white solid was recrystallized from acetonitrile, so that 4.4 g of a photobase generator (2-5)

of the present invention (white solid) was obtained. As a result of an analysis by $^1$H-NMR {300 MHz, DMSO-d6, δ (ppm): 8.9 (s, 1H), 8.7 (d, 2H), 8.2 (d, 2H), 7.7 (t, 2H), 7.6 (t, 2H), 7.3-7.1 (m, 8H), 7.0-6.9 (m, 8H), 6.9-6.8 (m, 4H), 5.6 (s, 2H), 3.6-3.4 (m, 6H), 1.9 (m, 1H), 1.8-1.6 (m, 6H)}, it was confirmed that this white solid was 9-anthrylmethyl-1-azabicyclo[2.2.2]octanium tetraphenylborate.

Example 4

Synthesis of 8-(9-oxo-9H-thioxanthen-4-yl)methyl-1,8-diazabicyclo[5.4.0]-7-undecenium tetraphenylborate {a photobase generator represented by chemical formula (1-2)}

(1) Synthesis of 2-(2-methylphenylthio)benzoic acid (intermediate 40)

A 100-ml eggplant flask was charged with 2.5 g of 2-methylthiophenol (Tokyo Chemical Industry Co., Ltd.), 3.3 g of 2-chlorobenzoic acid (Tokyo Chemical Industry Co., Ltd.), and 60 ml of N,N-dimethylformamide, and 2.4 g of potassium hydroxide and 0.6 g of a copper powder were added thereto. Heat was added up to 130° C. in an oil bath, followed by stirring for 5 hours and then cooling to room temperature (about 25° C.), so that a reaction liquid was obtained. While stirring 200 g of water contained in a 500-ml Erlenmeyer flask, the reaction liquid was added slowly, and 25 g of 5% hydrochloric acid was further added. After stirring for 30 minutes, extraction with 110 g of diethyl ether was performed twice. The ether layer was washed with 50 g of 5% hydrochloric acid and further washed with 60 g of water three times. The solvent of the ether layer was condensed with an evaporator, so that 2.2 g of intermediate (40) (white solid) was obtained. As a result of an analysis by $^1$H-NMR {300 MHz, DMSO-d6, δ (ppm): 13.5-12.9 (br, 1H), 7.9 (d, 1H), 7.5 (d, 1H), 7.4 (d, 2H), 7.4-7.3 (m, 2H), 7.2 (t, 2H), 6.5 (d, 2H), 2.2 (s, 3H)}, it was confirmed that this intermediate (40) (white solid) was 2-(2-methylphenylthio)benzoic acid.

Synthesis of (2) 4-methylthioxanthone (intermediate 41)

A 100-ml screw tube was charged with 5.0 g of intermediate (40) (2-(2-methylphenylthio)benzoic acid) and 50 g of sulfuric acid, which were stirred at 60° C. for 7 hours, so that a reaction liquid was obtained. While stirring 300 g of ice water contained in a 500-ml beaker, the reaction liquid was added slowly (a resinous material precipitated) and 180 g of dichloromethane was added thereto. The resinous material was dissolved by stirring for additional 30 minutes, and then the aqueous layer was separated by a separatory operation. The aqueous layer was neutralized with 48% aqueous potassium hydroxide solution. To the aqueous layer was added 200 g of dichloromethane, and extraction was performed. The extract was combined with organic layer, washed with 10% aqueous potassium hydroxide solution, and further washed with 130 g of water three times. Subsequently, the organic layer was dried over anhydrous sodium sulfate and then the solvent was distilled away, so that 3.2 g of intermediate (41) (yellow-orange solid) was obtained. As a result of an analysis by $^1$H-NMR {300 MHz, DMSO-d6, δ (ppm): 8.4 (d, 1H), 8.3 (d, 1H), 7.9 (d, 1H), 7.8 (t, 1H), 7.7 (d, 1H), 7.6 (t, 1H), 7.5 (t, 1H), 2.5 (s, 3H)}, it was confirmed that this intermediate (41) (yellow-orange solid) was 4-methylthioxanthone.

(3) Synthesis of 4-bromomethylthioxanthone (intermediate 42)

In the same manner as in Example 1 except for changing "2.1 g of intermediate (10) (methylthioxanthone mixture)" to "2.9 g of intermediates (41) (4-methylthioxanthone)", 1.6 g of intermediate (42) (pale brown solid) was obtained. As a result of analysis by $^1$H-NMR {300 MHz, DMSO-d6, δ (ppm): 8.7 (d, 1H), 8.6 (s, 1H), 7.8-7.6 (m, 4H), 7.5 (t, 1H), 4.6 (s, 2H)}, it was confirmed that this intermediate (42) (pale brown solid) was 4-bromomethylthioxanthone.

(4) Synthesis of 8-(9-oxo-9H-thioxanthen-4-yl)methyl-1,8-diazabicyclo[5.4.0]-7-undecenium bromide (intermediate 43)

In the same manner as in Example 1 except for changing "1.0 g of intermediate (11) (2-bromomethylthioxanthone)" to "1.5 g of intermediates (42) (4-bromomethylthioxanthone)", 1.8 g of intermediate (43) (pale yellow solid) was obtained. As a result of an analysis by $^1$M-NMR {300 MHz, CDCl$_3$, δ (ppm): 8.6 (d, 1H), 8.3 (s, 1H), 7.8 (d, 1H), 7.7-7.6 (m, 3H), 7.5 (t, 1H), 5.1 (s, 2H), 3.8 (m, 6H), 3.1-2.9 (m, 2H), 2.3-2.1 (m, 2H), 2.0-1.7 (m, 6H)}, it was confirmed that this intermediate (43) (pale yellow solid) was 8-(9-oxo-9H-thioxanthen-4-yl)methyl-1,8-diazabicyclo[5.4.0]-7-undecenium bromide.

(5) Synthesis of 8-(9-oxo-9H-thioxanthen-4-yl)methyl-1,8-diazabicyclo[5.4.0]-7-undecenium tetraphenylborate In the same manner as in Example 1 except for changing "1.0 g of intermediate (12) (8-(9-oxo-9H-thioxanthen-2-yl)methyl-1,8-diazabicyclo[5.4.0]-7-undecenium bromide" to "1.5 g of intermediate (43) (8-(9-oxo-9H-thioxanthen-4-yl)methyl-1,8-diazabicyclo[5.4.0]-7-undecenium bromide", 1.9 g of a photobase generator (1-2) of the present invention (pale yellow solid) was obtained. As a result of an analysis by $^1$H-NMR {300 MHz, DMSO-d6, δ ppm}: 8.5 (m, 2H), 8.0-7.8 (m, 2H), 7.7-7.6 (m, 3H), 7.3-7.1 (m, 8H), 7.0-6.8 (m, 8H), 6.8-6.7 (m, 4H), 5.0 (s, 2H), 3.8-3.4 (m, 6H), 2.9-2.8 (m, 2H), 2.2-2.0 (m, 2H), 1.7-1.5 (m, 6H)}, it was confirmed that this pale yellow solid was 8-(9-oxo-9H-thioxanthen-4-yl)methyl-1,8-diazabicyclo[5.4.0]-7-undecenium tetraphenylborate.

Example 5

Synthesis of 8-(7-methoxy-9-oxo-9H-thioxanthen-2-yl)methyl-1,8-diazabicyclo[5.4.0]-7-undecenium tetraphenylborate {a photobase generator represented by chemical formula (1-3)}

(1) Synthesis of 2-(4-methylphenylthio)-5-methoxybenzoic acid (intermediate 50)

In the same manner as in Example 4 except for changing "2.5 g of 2-methylthiophenol" to "2.5 g of 4-methylthiophenol (Tokyo Chemical Industry Co., Ltd.)", and "3.3 g of 2-chlorobenzoic acid" to "4.9 g of 2-bromo-5-methoxybenzoic acid (Tokyo Chemical Industry Co., Ltd.), 5.6 g of intermediates (50) (white solid) was obtained. As a result of an analysis by $^1$H-NMR {300 MHz, DMSO-d6, δ (ppm): 13.5-12.9 (br, 1H), 7.4 (s, 1H), 7.3 (d, 2H), 7.2 (d, 2H), 7.0 (d, 1H), 6.8 (d, 1H), 3.7 (s, 3H), 2.3 (s, 3H)}, it was confirmed that this intermediate (50) (white solid) was 2-(4-methylphenylthio)-5-methoxybenzoic acid.

(2) Synthesis of 2-methyl-7-methoxythioxanthone (intermediate 51)

In the same manner as in Example 4 except for changing "5.0 g of intermediate (40) (2-(2-methylphenylthio)benzoic acid)" to "5.6 g of intermediate (50) (2-(4-methylphenylthio)-5-methoxybenzoic acid)", 3.2 g of intermediate (51) (yellow solid) was obtained. As a result of an analysis by $^1$H-NMR {300 MHz, DMSO-d6, δ (ppm): 8.2 (s, 1H), 7.9 (s, 1H), 7.7-7.6 (m, 2H), 7.5 (d, 1H), 7.3 (d, 1H), 3.8 (s, 3H), 2.4 (s, 3H)}, it was confirmed that this intermediate (51) (white solid) was 2-methyl-7-methoxythioxanthone.

(3) Synthesis of 2-bromomethyl-7-methoxythioxanthone (intermediate 52)

In the same manner as in Example 1 except for changing "2.1 g of intermediate (10) (methylthioxanthone mixture)" to "3.0 g of intermediate (51) (2-methyl-7-methoxythioxanthone)", and "ethyl acetate" to "acetone" as a recrystallization solvent, 2.0 g of intermediate (52) (pale yellow solid) was obtained. As a result of an analysis by $^1$H-NMR {300 MHz, DMSO-d6, δ (ppm): 8.5 (s, 1H), 7.9 (d, 1H), 7.8 (m, 3H), 7.5 (m, 1H), 4.9 (s, 2H), 3.9 (s, 3H)}, it was confirmed that this intermediate (52) (pale yellow solid) was 2-bromomethyl-7-methoxythioxanthone.

(4) Synthesis of 8-(7-methoxy-9-oxo-9H-thioxanthen-2-yl)methyl-1,8-diazabicyclo[5.4.0]-7-undecenium bromide (intermediate 53)

In the same manner as in Example 1 except for changing "1.0 g of intermediate (11) (2-bromomethylthioxanthone)" to "2.0 g of intermediate (52) (2-bromomethyl-7-methoxythioxanthone)", 2.7 g of intermediate (53) (yellow-brown solid) was obtained. As a result of an analysis by $^1$H-NMR {300 MHz, DMSO-d6, δ (ppm): 8.4 (s, 1H), 8.0-7.9 (m, 2H), 7.8 (d, 1H), 7.7 (d, 1H), 7.5 (d, 1H), 5.0 (s, 2H), 3.9 (s, 3H), 3.7 (m, 2H), 3.6-3.5 (m, 4H), 3.0-2.9 (m, 2H), 2.1-2.0 (m, 2H), 1.7-1.5 (m, 6H)}, it was confirmed that this intermediate (53) (yellow-brown solid) was 8-(7-methoxy-9-oxo-9H-thioxanthen-2-yl)methyl-1,8-diazabicyclo[5.4.0]-7-undecenium bromide.

(5) Synthesis of 8-(7-methoxy-9-oxo-9H-thioxanthen-2-yl)methyl-1,8-diazabicyclo[5.4.0]-7-undecenium tetraphenylborate In the same manner as in Example 1 except for changing "1.0 g of intermediate (12) (8-(9-oxo-9H-thioxanthen-2-yl)methyl-1,8-diazabicyclo[5.4.0]-7-undecenium bromide" to "2.7 g of intermediate (53) (8-(7-methoxy-9-oxo-9H-thioxanthen-2-yl)methyl-1,8-diazabicyclo[5.4.0]-7-undecenium bromide", 3.9 g of a photobase generator (1-3) of the present invention (yellow solid) was obtained. As a result of an analysis by $^1$H-NMR {300 MHz, DMSO-d6, δ (ppm): 8.4 (s, 1H), 8.0-7.9 (m, 2H), 7.8 (d, 1H), 7.7 (m, 1H), 7.5 (d, 1H), 7.3-7.1 (m, 8H), 7.0-6.8 (m, 8H), 6.8-6.7 (m, 4H), 5.0 (s, 2H), 3.9 (s, 3H), 3.7-3.6 (m, 2H), 3.6-3.4 (m, 4H), 2.1-1.9 (m, 2H), 1.8-1.4 (m, 6H)}, it was confirmed that this yellow solid was 8-(7-methoxy-9-oxo-9H-thioxanthen-2-yl)methyl-1,8-diazabicyclo[5.4.0]-7-undecenium tetraphenylborate.

Example 6

Synthesis of 8-(2-methoxy-9-oxo-9H-thioxanthen-4-yl)methyl-1,8-diazabicyclo[5.4.0]-7-undecenium tetraphenylborate {a photobase generator represented by chemical formula (1-4)}

(1) Synthesis of 2-methoxy-4-methylthioxanthone (intermediate 60)

In the same manner as in Example 1 except for changing "25 g of toluene" to "32 g of m-methylanisole (Wako Pure Chemical Industries, Ltd.)", 3.4 g of intermediate (60) (yellow solid) was obtained. As a result of an analysis by $^1$H-NMR {300 MHz, DMSO-d6, δ (ppm): 8.5 (s, 1H), 7.9-7.7 (m, 3H), 7.6 (t, 1H), 7.3 (s, 1H), 3.9 (s, 3H), 2.4 (s, 3H)}, it was confirmed that this intermediate (60) (yellow solid) was 2-methoxy-4-methylthioxanthone.

(2) Synthesis of 4-bromomethyl-2-methoxythioxanthone (intermediate 61)

In the same manner as in Example 1 except for changing "2.1 g of intermediate (10) (methylthioxanthone mixture)" to "1.5 g of intermediate (60) (2-methoxy-4-methylthioxanthone)", and "ethyl acetate" to "2-butanone" as a recrystallization solvent, 0.7 g of intermediate (61) (pale yellow solid) was obtained. As a result of an analysis by $^1$H-NMR {300 MHz, CDCl$_3$, δ (ppm): 8.6 (d, 1H), 8.1 (s, 1H), 7.7 (m, 2H), 7.5 (m, 1H), 7.4 (s, 1H), 4.7 (s, 2H), 4.0 (s, 3H)}, it was confirmed that this intermediate (61) (pale yellow solid) was 4-bromomethyl-2-methoxythioxanthone.

(3) Synthesis of 8-(2-methoxy-9-oxo-9H-thioxanthen-4-yl)methyl-1,8-diazabicyclo[5.4.0]-7-undecenium bromide (intermediate 62)

In the same manner as in Example 1 except for changing "1.0 g of intermediate (11) (2-bromomethylthioxanthone)" to "0.7 g of intermediate (61) (4-bromomethyl-2-methoxythioxanthone)", 0.8 g of intermediate (62) (yellowish white solid) was obtained. As a result of an analysis by $^1$H-NMR {300 MHz, DMSO-d6, δ (ppm): 8.5 (d, 1H), 8.0-7.9 (m, 2H), 7.8 (t, 1H), 7.6 (t, 1H), 7.3 (s, 1H), 5.0 (s, 2H), 4.0 (s, 3H), 3.8-3.4 (m, 6H), 2.9-2.8 (m, 2H), 2.2-2.0 (m, 2H), 1.8-1.5 (m, 6H)}, it was confirmed that this intermediate (62) (yellowish white solid) was 8-(2-methoxy-9-oxo-9H-thioxanthen-4-yl)methyl-1,8-diazabicyclo[5.4.0]-7-undecenium bromide.

(4) Synthesis of 8-(2-methoxy-9-oxo-9H-thioxanthen-4-yl)methyl-1,8-diazabicyclo[5.4.0]-7-undecenium tetraphenylborate In the same manner as in Example 1 except for changing "1.0 g of intermediate (12) (8-(9-oxo-9H-thioxanthen-2-yl)methyl-1,8-diazabicyclo[5.4.0]-7-undecenium bromide" to "0.7 g of intermediate (62) (8-(2-methoxy-9-oxo-9H-thioxanthen-4-yl)methyl-1,8-diazabicyclo[5.4.0]-7-undecenium bromide", 0.8 g of a photobase generator (1-4) of the present invention (yellow solid) was obtained. As a result of an analysis by $^1$H-NMR {300 MHz, DMSO-d6, δ (ppm): 8.5 (d, 1H), 8.0 (s, 1H), 7.9 (d, 1H), 7.8 (t, 1H), 7.6 (t, 1H), 7.3 (s, 1H), 7.2-7.1 (m, 8H), 7.0-6.8 (m, 8H), 6.8-6.7 (m, 4H), 5.0 (s, 2H), 4.0 (s, 3H), 3.8-3.4 (m, 6H), 2.9-2.8 (m, 2H), 2.2-2.0 (m, 2H), 1.8-1.5 (m, 6H)}, it was confirmed that this yellow solid was 8-(2-methoxy-9-oxo-9H-thioxanthen-4-yl)methyl-1,8-diazabicyclo[5.4.0]-7-undecenium tetraphenylborate.

Example 7

Synthesis of 8-(2-methoxy-9-oxo-9H-thioxanthen-3-yl)methyl-1,8-diazabicyclo[5.4.0]-7-undecenium tetraphenylborate {a photobase generator represented by chemical formula (1-5)}

(1) Synthesis of 2-methoxy-3-methylthioxanthone (intermediate 70)

In the same manner as in Example 1 except for changing "25 g of toluene" to "32 g of 2-methylanisole (Tokyo Chemical Industry Co., Ltd.)", 5.0 g of intermediate (70) (yellow solid) was obtained. As a result of an analysis by $^1$H-NMR {300 MHz, DMSO-d6, δ (ppm): 8.5 (d, 1H), 7.9-7.8 (m, 2H), 7.8-7.7 (t, 1H), 7.7-7.6 (s, 1H), 7.6-7.5 (t, 1H), 3.9 (s, 3H), 2.3 (s, 3H)} it was confirmed that this intermediate (70) (yellow solid) was 2-methoxy-3-methylthioxanthone.

(2) Synthesis of 3-bromomethyl-2-methoxythioxanthone (intermediate 71)

In the same manner as in Example 1 except for changing "2.1 g of intermediate (10) (methylthioxanthone mixture)" to "0.08 g of intermediate (71) (2-methoxy-3-methylthioxanthone)", 0.11 g of intermediate (71) (yellow solid) was obtained. As a result of an analysis by $^1$H-NMR {300 MHz, CDCl$_3$, δ (ppm): 8.6 (d, 1H), 8.1 (s, 1H), 7.6-7.4 (m, 4H), 4.6 (s, 2H), 4.0 (s, 3H)}, it was confirmed that this intermediate (71) (yellow solid) was 3-bromomethyl-2-methoxythioxanthone.

(3) Synthesis of 8-(2-methoxy-9-oxo-9H-thioxanthen-3-yl)methyl-1,8-diazabicyclo[5.4.0]-7-undecenium tetraphenylborate In 5 ml of chloroform was dissolved 0.11 g of intermediate (71) (3-bromomethyl-2-methoxythioxanthone), and 0.04 g of 1,8-diazabicyclo[5.4.0]-7-undecene was dropped thereto. Then a reaction was performed at 50° C. for 4 hours, so that a reaction liquid was obtained. The reaction liquid was dropped slowly into an aqueous solution composed of 0.1 g of sodium tetraphenylborate and 2.5 g of water and further stirred at room temperature (about 25° C.) for 1 hour. Then the aqueous layer was removed by a separatory operation and the organic layer was washed with water three times. The organic layer was condensed with an evaporator, so that 0.24 g of a yellow solid was obtained. This yellow solid was recrystallized from acetonitrile, so that 0.13 g of a photobase generator (1-5) of the present invention (yellow powder) was obtained. As a result of an analysis by $^1$H-NMR {300 MHz, DMSO-d6, δ (ppm): 8.5 (d, 1H), 8.0 (s, 1H), 7.8-7.7 (m, 2H), 7.7 (s, 1H), 7.6 (t, 1H), 7.2-7.1 (m, 8H), 7.0-6.8 (m, 8H), 6.8-6.7 (m, 4H), 4.9 (s, 2H), 4.0 (s, 3H), 3.8-3.4 (m, 6H), 2.9-2.8 (m, 2H), 1.8-1.5 (m, 8H)}, it was confirmed that this yellow powder was 8-(2-methoxy-9-oxo-9H-thioxanthen-3-yl)methyl-1,8-diazabicyclo[5.4.0]-7-undecenium tetraphenylborate.

Example 8

Synthesis of 8-(2,3-dimethoxy-9-oxo-9H-thioxanthen-4-yl)methyl-1,8-diazabicyclo[5.4.0]-7-undecenium tetraphenylborate {a photobase generator represented by chemical formula (1-6)}

(1) Synthesis of 2,3-dimethoxy-4-methylthioxanthone (intermediate 80)

In the same manner as in Example 1 except for changing "25 g of toluene" to "4.0 g of 2,3-dimethoxytoluene (1-methyl-2,3-dimethoxybenzene, Aldrich)", 0.6 g of intermediate (80) (yellow solid) was obtained. As a result of an analysis by $^1$H-NMR {300 MHz, DMSO-d6, δ (ppm): 8.5-8.4 (d, 1H), 8.0-7.8 (m, 2H), 7.8-7.7 (t, 1H), 7.6 (t, 1H), 4.0 (s, 3H), 3.9 (s, 3H), 2.4 (s, 3H)}, it was confirmed that this intermediate (80) (yellow solid) was 2,3-dimethoxy-4-methylthioxanthone.

(2) Synthesis of 4-bromomethyl-2,3-dimethoxythioxanthone (intermediate 81)

In the same manner as in Example 1 except for changing "2.1 g of intermediate (10) (methylthioxanthone mixture)" to "0.09 g of intermediate (80) (2,3-dimethoxy-4-methylthioxanthone)", 0.12 g of intermediate (81) (yellow solid) was obtained. As a result of an analysis by $^1$H-NMR {300 MHz, CDCl$_3$, δ (ppm): 8.6 (d, 1H), 8.2 (s, 1H), 7.7-7.6 (m, 2H), 7.5 (m, 1H), 4.8 (s, 2H), 4.1 (s, 3H), 4.0 (s, 3H)}, it was confirmed that this intermediate (81) (yellow solid) was 4-bromomethyl-2,3-dimethoxythioxanthone.

(3) Synthesis of 8-(2,3-dimethoxy-9-oxo-9H-thioxanthen-4-yl)methyl-1,8-diazabicyclo[5.4.0]-7-undecenium tetraphenylborate In the same manner as in Example 7 except for changing "0.11 g of intermediate (71) (3-bromomethyl-2-methoxythioxanthone)" to "0.12 g of intermediate (81) (4-bromomethyl-2,3-dimethoxythioxanthone)", 0.13 g of a photobase generator (1-6) (yellow powder) of the present invention was obtained. As a result of an analysis by $^1$H-NMR {300 MHz, DMSO-d6, δ (ppm): 8.5 (d, 1H), 8.2 (s, 1H), 7.9-7.8 (m, 3H), 7.6 (t, 1H), 7.2-7.1 (m, 8H), 7.0-6.8 (m, 8H), 6.8-6.7 (m, 4H), 5.1 (s, 2H), 4.0 (s, 3H), 3.9 (s, 3H), 3.8-3.4 (m, 6H), 2.7-2.6 (m, 2H), 2.0-1.8 (m, 2H), 1.8-1.6 (m, 6H)}, it was confirmed that this yellow powder was 8-(2,3-dimethoxy-9-oxo-9H-thioxanthen-4-yl)methyl-1,8-diazabicyclo[5.4.0]-7-undecenium tetraphenylborate.

Example 9

Synthesis of 8-(2-acetoxy-9-oxo-9H-thioxanthen-4-yl)methyl-1,8-diazabicyclo[5.4.0]-7-undecenium tetraphenylborate {a photobase generator represented by chemical formula (1-7)}

(1) Synthesis of 2-hydroxy-4-methylthioxanthone (intermediate 90)

In the same manner as in Example 1 except for changing "25 g of toluene" to "29 g of m-cresol (Wako Pure Chemical Industries, Ltd.)", 3.2 g of intermediate (90) (yellow-green solid) was obtained. As a result of an analysis by $^1$H-NMR {300 MHz, DMSO-d6, δ (ppm): 10.0 (s, 1H), 8.4 (d, 1H), 7.9-7.7 (m, 3H), 7.6 (t, 1H), 7.2 (s, 1H), 2.4 (s, 3H)}, it was confirmed that this intermediate (90) (yellow-green solid) was 2-hydroxy-4-methylthioxanthone.

(2) Synthesis of 2-acetoxy-4-methylthioxanthone (intermediate 91)

To a 200-ml eggplant flask were charged 1.2 g of intermediate (91) (2-hydroxy-4-methylthioxanthone), 78 g of tetrahydrofuran, and 0.6 g of potassium tert-butoxide (Nacalai Tesque, Inc.), which were dissolved. Then 1.1 g of acetylchloride (Wako Pure Chemical Industries, Ltd.) was added thereto and a reaction was performed for 1 hour, and subsequently the solvent was distilled away, so that 1.8 g of a yellowish white solid was obtained. This yellowish white solid was dissolved in a mixed solvent composed of 72 g of chloroform and 22 g of tetrahydrofuran and it was washed with 50 g of water three times. Then the organic solvent was concentrated and a precipitated solid was recrystallized from methanol, so that 1.2 g of intermediate (91) (yellowish white solid) was obtained. As a result of an analysis by $^1$H-NMR {300 MHz, DMSO-d6, δ (ppm): 8.4 (d, 1H), 8.0 (s, 1H), 7.9-7.7 (m, 2H), 7.6 (t, 1H), 7.5 (s, 1H), 2.5 (s, 3H), 2.3 (s, 3H)}, it was confirmed that this intermediate (91) (yellowish white solid) was 2-acetoxy-4-methylthioxanthone.

(3) Synthesis of 2-acetoxy-4-bromomethylthioxanthone (intermediate 92)

In the same manner as in Example 1 except for changing "2.1 g of intermediate (10) (methylthioxanthone mixture)" to "1.1 g of intermediate (91) (2-acetoxy-4-methylthioxanthone)", 1.0 g of intermediate (92) (yellow solid) was obtained. As a result of an analysis by $^1$H-NMR {300 MHz, DMSO-d6, δ (ppm): 8.4 (d, 1H), 8.2 (s, 1H), 8.0-7.8 (m, 3H), 7.6 (t, 1H), 5.0 (s, 2H), 2.3 (s, 3H)}, it was confirmed that this intermediate (92) (yellow solid) was 2-acetoxy-4-bromomethylthioxanthone.

(4) Synthesis of 8-(2-acetoxy-9-oxo-9H-thioxanthen-4-yl)methyl-1,8-diazabicyclo[5.4.0]-7-undecenium bromide (intermediate 93)

In the same manner as in Example 1 except for changing "0.7 g of intermediate (11) (2-bromomethylthioxanthone)" to "0.48 g of intermediate (92) (2-acetoxy-4-bromomethylthioxanthone)", 0.75 g of intermediate (93) (yellow-brown solid) was obtained. As a result of an analysis by $^1$H-NMR {300 MHz, DMSO-d6, δ (ppm): 8.5 (d, 1H), 8.2 (s, 1H), 8.0 (d, 1H), 7.9 (t, 1H), 7.7 (t, 1H), 7.6 (s, 1H), 5.1 (s, 2H), 3.8-3.5 (m, 8H), 2.9 (m, 2H), 2.5 (s, 3H), 2.2 (m, 2H), 1.8-1.4 (m, 6H)}, it was confirmed that this intermediate (93) (yellow-brown solid) was 8-(2-acetoxy-9-oxo-9H-thioxanthen-4-yl)methyl-1,8-diazabicyclo[5.4.0]-7-undecenium bromide.

(5) Synthesis of 8-(2-acetoxy-9-oxo-9H-thioxanthen-4-yl)methyl-1,8-diazabicyclo[5.4.0]-7-undecenium tetraphenylborate In the same manner as in Example 1 except for changing "1.0 g of intermediate (12) (8-(9-oxo-9H-thioxanthen-2-yl) methyl-1,8-diazabicyclo[5.4.0]-7-undecenium bromide" to "1.6 g of intermediate (93) (8-(2-acetoxy-9-oxo-9H-thioxanthen-4-yl)methyl-1,8-diazabicyclo[5.4.0]-7-undecenium bromide", and "acetonitrile/ether" to "methanol" as a recrystallization solvent, 1.2 g of a photobase generator (1-7) of the present invention (yellow solid) was obtained. As a result of an analysis by $^1$H-NMR {300 MHz, DMSO-d6, δ (ppm): 8.5 (d, 1H), 8.2 (s, 1H), 8.0 (d, 1H), 7.9 (t, 1H), 7.7 (t, 1H), 7.5 (s, 1H), 7.2-7.1 (m, 8H), 7.0-6.9 (m, 8H), 7.8-7.7 (m, 4H), 5.1 (s, 2H), 3.8-3.4 (m, 6H), 2.8 (m, 2H), 2.4 (s, 3H), 2.1-2.0 (m, 2H), 1.8-1.5 (m, 6H)}, it was confirmed that this yellow solid was 8-(2-acetoxy-9-oxo-9H-thioxanthen-4-yl)methyl-1,8-diazabicyclo[5.4.0]-7-undecenium tetraphenylborate.

Example 10

Synthesis of 8-(2-hydroxy-9-oxo-9H-thioxanthen-4-yl)methyl-1,8-diazabicyclo[5.4.0]-7-undecenium tetraphenylborate {a photobase generator represented by chemical formula (1-8)}

To a 200-ml eggplant flask was charged 2.9 g of intermediate (93) (8-(2-acetoxy-9-oxo-9H-thioxanthen-4-yl)methyl-1,8-diazabicyclo[5.4.0]-7-undecenium bromide), and 100 g of water and 2 g of 10% hydrochloric acid were added thereto and a reaction was performed at 60° C. for 10 hours. Then neutralization was performed by adding 9.1 g of saturated aqueous sodium hydrogen carbonate solution, and subsequently an aqueous solution composed of 1.8 g of sodium tetraphenylborate and 37 g of water was added and stirred for 30 minutes. A precipitated yellow solid was collected by filtration and washed with chloroform repeatedly, so that 1.8 g of a photobase generator (1-8) of the present invention (yellow solid) was obtained. As a result of an analysis by $^1$H-NMR {300 MHz, DMSO-d6, δ (ppm): 10.7-10.0 (br, 1H), 8.5 (d, 1H), 8.0-7.9 (m, 2H), 7.8 (t, 1H), 7.5 (t, 1H), 7.2-7.1 (m, 8H), 7.0-6.9 (m, 8H), 7.8-7.7 (m, 4H), 5.0 (s, 2H), 3.8-3.5 (m, 6H), 2.9-2.8 (m, 2H), 2.1-2.0 (m, 2H), 1.8-1.5 (m, 6H)}, it was confirmed that this yellow solid was 8-(2-hydroxy-9-oxo-9H-thioxanthen-4-yl)methyl-1,8-diazabicyclo[5.4.0]-7-undecenium tetraphenylborate.

Example 11

Synthesis of 8-(9-anthrylmethyl)-1,8-diazabicyclo[5.4.0]-7-undecenium tetraphenylborate {a photobase generator represented by chemical formula (2-1)}

In the same manner as in Example 3 except for changing "1.0 g of 1-azabicyclo[2.2.2]octane" to "1.3 g of 1,8-diazabicyclo[5.4.0]-7-undecene", 4.7 g of a photobase generator (2-1) of the present invention (white solid) was obtained. As a result of an analysis by $^1$H-NMR {300 MHz, DMSO-d6, δ (ppm): 8.8 (s, 1H), 8.3-8.1 (m, 4H), 7.8-7.5 (m, 4H), 7.2-7.1 (m, 8H), 7.0-6.8 (m, 8H), 7.8-7.7 (m, 4H), 5.9 (s, 2H), 3.8-3.7 (m, 2H), 3.5-3.2 (m, 6H), 2.8 (m, 2H), 2.0-1.6 (m, 8H)}, it was confirmed that this white solid was 8-(9-anthrylmethyl)-1,8-diazabicyclo[5.4.0]-7-undecenium tetraphenylborate.

Example 12

Synthesis of 8-(10-acetyl-9-anthrylmethyl)-1,8-diazabicyclo[5.4.0]-7-undecenium tetraphenylborate {a photobase generator represented by chemical formula (2-3)}

(1) Synthesis of 9-acetyl-10-methylanthracene (intermediate 120)

A 100-ml eggplant flask was charged with 4.8 g of 9-methylanthracene (Aldrich), 7.7 g of acetic anhydride (Wako Pure Chemical Industries, Ltd.), and 28.2 g of acetonitrile, and methanesulfonic acid (Wako Pure Chemical Industries, Ltd.) was added thereto. A reaction was performed at 65° C. for 16 hours, so that a reaction liquid was obtained. To a 300-ml Erlenmeyer flask was charged with 75 g of water, and the reaction liquid was poured thereto and 150 g of dichloromethane was added. After stirring for 15 minutes, the aqueous layer was removed by separation. Further, the organic layer was washed with 80 g of water three times and then concentrated with an evaporator, so that 5.7 g of a brown solid was obtained. This brown solid was recrystallized from dichloromethane/hexane, so that 3.3 g of intermediate (120) (dark red solid) was obtained. As a result of an analysis by $^1$H-NMR {300 MHz, CDCl$_3$, δ (ppm): 8.4 (m, 2H), 7.9 (m, 2H), 7.6-7.5 (m, 4H), 3.1 (s, 3H), 2.8 (s, 3H)}, it was confirmed that this intermediate (120) (dark red solid) was 9-acetyl-10-methylanthracene.

(2) Synthesis of 9-acetyl-10-bromomethylanthracene (intermediate 121)

In the same manner as in Example 1 except for changing "2.1 g of intermediate (10) (methylthioxanthone mixture)" to "0.17 g of intermediate (120) (9-acetyl-10-methylanthracene)" and "8.3 g of N-bromosuccinimide (Wako Pure Chemical Industries, Ltd.)" to "0.13 g of N-bromosuccinimide (Wako Pure Chemical Industries, Ltd.)", 0.12 g of intermediate (121) (yellow solid) was obtained. As a result of an analysis by $^1$H-NMR {300 MHz, CDCl$_3$, δ (ppm): 8.4 (2H, d), 7.9 (2H, d), 7.7 (t, 2H), 7.6 (t, 2H), 5.5 (s, 2H), 2.8 (s, 3H)}, it was confirmed that this intermediate (121) (yellow solid) was 9-acetyl-10-bromomethylanthracene.

(3) Synthesis of 8-(10-acetyl-9-anthrylmethyl)-1,8-diazabicyclo[5.4.0]-7-undecenium tetraphenylborate In the same manner as in Example 7 except for changing "0.11 g of intermediate (71) (3-bromomethyl-2-methoxythioxanthone)" to "3.1 g of intermediate (121) (9-acetyl-10-bromomethylanthracene)", 3.8 g of a photobase generator (2-3) of the present invention (yellow powder) was obtained. As a result of an analysis by $^1$H-NMR {300 MHz, DMSO-d6, δ (ppm): 8.4 (d, 2H), 7.9 (d, 2H), 7.8-7.6 (m, 4H), 7.3-7.1 (m, 8H), 7.0-6.8 (m, 8H), 6.8-6.7 (m, 4H), 5.9 (s, 2H), 3.8-3.7 (m, 2H), 3.5-3.3 (m, 6H), 2.9 (s, 3H), 2.8-2.7 (m, 2H), 1.9-1.6 (m, 8H)}, it was confirmed that this yellow powder was 8-(10-acetyl-9-anthrylmethyl-1,8-diazabicyclo[5.4.0]-7-undecenium tetraphenylborate.

Example 13

Synthesis of 8-(10-benzoyl-9-anthrylmethyl)-1,8-diazabicyclo[5.4.0]-7-undecenium tetraphenylborate {a photobase generator represented by chemical formula (2-4)}

(1) Synthesis of 9-benzoyl-10-methylanthracene (intermediate 130)

A four-necked, 100-ml flask was purged with nitrogen, and 4.2 g of aluminium chloride (Wako Pure Chemical Industries, Ltd.) and 50 g of dichloromethane were charged thereto and cooled to 5° C. in an ice bath. A solution composed of 4.5 g of benzoyl chloride (Nacalai Tesque, Inc.) and 30 g of dichloromethane was dropped slowly so that the temperature would not exceed 5° C. After stirring for 30 minutes, a solution composed of 6.1 g of 9-methylanthracene (Aldrich) and 10 g of dichloromethane was dropped so that the temperature would not exceed 5° C., and the a reaction was performed for 5 hours. Subsequently, 50 g of 5% hydrochloric acid was dropped while the reaction liquid was being cooled, followed by transference to an Erlenmeyer flask. Then 50 g of dichloromethane and 30 g of 5% hydrochloric acid were added and stirred for 30 minutes, and the aqueous layer was removed by separation. The organic layer was washed with 20 g of water, and the organic layer was neutralized with a saturated aqueous sodium hydrogen carbonate solution and washed with 50 g of water twice. The organic layer was concentrated, so that a yellow solid was obtained.

The yellow solid was washed with ether, so that 6.9 g of intermediate (130) was obtained. As a result of an analysis by $^1$H-NMR {300 MHz, CDCl$_3$, δ (ppm): 8.4 (d, 2H), 7.8 (d, 2H), 7.7 (d, 2H), 7.6-7.5 (m, 3H), 7.4 (m, 4H), 3.2 (s, 3H)}, it was confirmed that this intermediate (130) (yellow solid) was 9-benzoyl-10-methyl anthracene.

(2) Synthesis of 9-benzoyl-10-bromomethylanthracene (intermediate 131)

In the same manner as in Example 1 except for changing "2.1 g of intermediate (10) (methylthioxanthone mixture)" to "3.6 g of intermediate (130) (9-benzoyl-10-methylanthracene)" and "8.3 g of N-bromosuccinimide (Wako Pure Chemical Industries, Ltd.)" to "0.13 g of N-bromosuccinimide (Wako Pure Chemical Industries, Ltd.)", 3.3 g of intermediate (131) (yellow solid) was obtained. As a result of an analysis by $^1$H-NMR {300 MHz, CDCl$_3$, δ (ppm): 8.4 (d, 2H), 7.9-7.7 (m, 4H), 7.7-7.5 (m, 3H), 7.5-7.3 (m, 4H), 5.6 (s, 2H)}, it was confirmed that this intermediate (131) (yellow solid) was 9-benzoyl-10-bromomethylanthracene.

(3) Synthesis of 8-(10-benzoyl-9-anthrylmethyl)-1,8-diazabicyclo[5.4.0]-7-undecenium tetraphenylborate In the same manner as in Example 7 except for changing "0.11 g of intermediate (71) (3-bromomethyl-2-methoxythioxanthone)" to "3.0 g of intermediate (131) (9-benzoyl-10-bromomethylanthracene)", 2.9 g of a photobase generator (2-4) of the present invention (yellow powder) was obtained. As a result of an analysis by $^1$H-NMR {300 MHz, DMSO-d6, δ (ppm): 8.4 (d, 2H), 7.8-7.6 (m, 7H), 7.6-7.4 (m, 4H), 7.3-7.1 (m, 8H), 7.0-6.8 (m, 8H), 6.8-6.7 (m, 4H), 6.0 (s, 2H), 3.9-3.7 (m, 2H), 3.5-3.4 (m, 4H), 3.0-2.8 (m, 2H), 2.0-1.6 (m, 8H)}, it was confirmed that this yellow powder was 8-(10-benzoyl-9-anthrylmethyl)-1,8-diazabicyclo[5.4.0]-7-undecenium tetraphenylborate.

Example 14

Synthesis of 1-(9-anthryl)methyl-3-hydroxy-1-azabicyclo[2.2.2]octanium tetraphenylborate {a photobase generator represented by chemical formula (2-6)}

In the same manner as in Example 3 except for changing "2.0 g of 1-azabicyclo[2.2.2]octane" to "1.1 g of 3-hydroxy-1-azabicyclo[2.2.2]octane (Aldrich)", 3.5 g of a photobase generator (2-6) of the present invention (white solid) was obtained. As a result of an analysis by $^1$H-NMR {300 MHz, DMSO-d6, δ (ppm): 8.9 (s, 1H), 8.7 (d, 2H), 8.2 (d, 2H), 7.7 (t, 2H), 7.6 (t, 2H), 7.2-7.0 (m, 8H), 7.0-6.9 (m, 8H), 6.9-6.8 (m, 4H), 5.7 (s, 2H), 5.5 (s, 1H), 4.2-4.1 (m, 1H), 3.6 (t, 1H), 3.4-3.2 (m, 4H), 3.0 (d, 1H), 2.2-1.6 (m, 5H)}, it was confirmed that this white solid was 1-(9-anthryl)methyl-3-hydroxy-1-azabicyclo[2.2.2]octanium tetraphenylborate.

Example 15

Synthesis of 5-(9-anthrylmethyl)-1,5-diazabicyclo[4.3.0]-5-nonenium tetraphenylborate {a photobase generator represented by chemical formula (2-7)}

In the same manner as in Example 3 except for changing "2.0 g of 1-azabicyclo[2.2.2]octane" to "1.1 g of 1,5-diazabicyclo[4.3.0]-5-nonene (San-Apro Ltd.)", 4.6 g of a photobase generator (2-7) of the present invention (white solid) was obtained. As a result of an analysis by $^1$H-NMR {300 MHz, DMSO-d6, δ (ppm): 8.8 (s, 1H), 8.3-8.1 (m, 4H), 7.8-7.5 (m, 4H), 7.2-7.1 (m, 8H), 7.0-6.8 (m, 8H), 6.8-6.7 (m, 4H), 5.7 (s, 2H), 3.8-3.7 (t, 2H), 3.5 (t, 2H), 3.4-3.2 (m, 2H), 2.7 (m, 2H), 2.2 (m, 2H), 1.7 (m, 2H)}, it was confirmed that this white solid was 5-(9-anthrylmethyl)-1,5-diazabicyclo[4.3.0]-5-nonenium tetraphenylborate: (2-7).

Example 16

Synthesis of 8-(9-anthrylmethyl)-1,8-diazabicyclo[5.4.0]-7-undecenium butyltriphenylborate {a photobase generator represented by chemical formula (2-8)}

In the same manner as in Example 3 except for changing "4.0 g of sodium tetraphenylborate" to "17.9 g of 20% aqueous lithium butyltriphenylborate solution (Hokko Chemical Industry Co., Ltd.)", 4.6 g of a photobase generator (2-8) of the present invention (yellowish white solid) was obtained. As a result of an analysis by $^1$H-NMR {300 MHz, DMSO-d6, δ (ppm): 8.8 (s, 1H), 8.3 (d, 2H), 8.2 (d, 2H), 7.7 (t, 2H), 7.6 (t, 2H), 7.3-7.1 (m, 6H), 7.0-6.8 (m, 6H), 6.8-6.7 (m, 3H), 5.9 (s, 2H), 3.8-3.7 (s, 2H), 3.5-3.3 (m, 6H), 2.8-2.7 (m, 2H), 1.9-1.6 (m, 8H), 1.3-1.1 (m, 2H), 1.0-0.7 (m, 7H)}, it was confirmed that this yellowish white solid was 8-(9-anthrylmethyl)-1,8-diazabicyclo[5.4.0]-7-undecenium butyltriphenylborate: (2-8).

Example 17

Synthesis of 8-(9-anthrylmethyl)-1,8-diazabicyclo[5.4.0]-7-undecenium benzoate {a photobase generator represented by chemical formula (2-9)}

In 40 g of methanol in a 50-ml eggplant flask was dissolved 2.0 g of 9-chloromethylanthracene (Aldrich), and 1.3 g of 1,8-diazabicyclo[5.4.0]-7-undecene was added thereto little by little (after the addition, some generation of heat was observed). Stirring was continued at room temperature (about 25° C.) for 1 hour, so that a reaction liquid was obtained. The reaction solution was dropped little by little to a dispersion liquid composed of 2.7 g of silver benzoate (Aldrich) and 20 g of methanol contained in a 100-ml eggplant flask and further was stirred at room temperature (about 25° C.) for 1 hour. Then a filtrate resulting from the removal of a formed gray solid was concentrated with an evaporator, so that 4.5 g of a brown solid was obtained. This brown solid was recrystallized from ether/hexane, so that 4.0 g of a photobase generator (2-9) of the present invention (brown solid) was obtained. As a result of an analysis by $^1$H-NMR {300 MHz, DMSO-d6, δ (ppm): 8.8 (s, 1H), 8.3 (d, 2H), 8.2 (d, 2H), 7.9 (m, 2H), 7.7 (t, 2H), 7.6 (t, 2H), 7.2 (m, 3H), 5.9 (s, 2H), 3.8-3.7 (m, 2H), 3.5-3.4 (m, 4H), 2.8-2.7 (m, 2H), 2.0-1.5 (m, 8H)}, it was confirmed that this brown solid was 8-(9-anthrylmethyl)-1,8-diazabicyclo[5.4.0]-7-undecenium benzoate: (2-9).

Example 18

Synthesis of 8-(9-anthrylmethyl)-1,8-diazabicyclo[5.4.0]-7-undecenium phenylglyoxylate: (2-10)

(1) Preparation of silver phenylglyoxylate

In 20 g of methanol was dissolved 3.9 g of phenylglyoxylic acid (Aldrich), and 0.9 g of sodium hydroxide (Wako Pure Chemical Industries, Ltd.) was added thereto little by little (generation of heat caused by neutralization was observed). After stirring for 1 hour, 10.4 g of 1 mol/L aqueous silver nitrate solution (Wako Pure Chemical Industries, Ltd.) was added thereto. Then a precipitated gray solid was collected by filtration, washed with methanol, and dried, so that 4.4 g of silver phenylglyoxylate (gray solid) was obtained.

(2) Synthesis of 8-(9-anthrylmethyl)-1,8-diazabicyclo[5.4.0]-7-undecenium phenylglyoxylate In the same manner as in Example 17 except for changing "2.7 g of silver benzoate" to "3.0 g of silver phenylglyoxylate", 2.6 g of a photobase generator (2-10) of the present invention (yellow solid) was obtained. As a result of an analysis by $^1$H-NMR {300 MHz, DMSO-d6, δ (ppm): 8.8 (s, 1H), 8.3 (d, 2H), 8.2 (d, 2H), 7.8 (d, 2H), 7.7 (t, 2H), 7.6 (t, 2H), 7.5 (d, 1H), 7.4 (t, 2H), 5.9 (s, 2H), 3.8-3.7 (m, 2H), 3.5-3.4 (m, 4H), 2.8-2.7 (m, 2H), 2.0-1.6 (m, 8H)}, it was confirmed that this yellow solid was 8-(9-anthrylmethyl)-1,8-diazabicyclo[5.4.0]-7-undecenium phenylglyoxylate: (2-10).

Example 19

Synthesis of N-(9-anthrylmethyl)-N,N,N-trioctylammonium tetraphenylborate: (2-11)

In the same manner as in Example 3 except for changing "1.0 g of 1-azabicyclo[2.2.2]octane" to "3.1 g of trioctylamine (Wako Pure Chemical Industries, Ltd.)", 6.2 g of a photobase generator (2-11) of the present invention (white solid) was obtained. As a result of an analysis by $^1$H-NMR {300 MHz, DMSO-d6, δ (ppm): 8.9 (s, 1H), 8.7 (d, 2H), 8.2 (d, 2H), 7.7 (t, 2H), 7.6 (t, 2H), 7.2-7.0 (m, 8H), 7.0-6.9 (m, 8H), 6.9-6.8 (m, 4H), 5.8 (s, 2H), 3.4-3.2 (m, 6H), 1.9-1.6 (m, 6H), 1.4-1.2 (m, 30H), 1.0-0.8 (t, 9H)}, it was confirmed that this white solid was N-(9-anthrylmethyl)-N,N,N-trioctylammonium tetraphenylborate: (2-11).

Comparative Example 1

Synthesis of 8-(4-benzoylphenyl)methyl-1,8-diazabicyclo[5.4.0]-7-undecenium phenylglyoxylate {a photobase generator represented by chemical formula (H1)}

(1) Synthesis of 4-bromomethylbenzophenone (intermediate H10)

To a 200-mL flask equipped with a reflux condenser were added 25.1 g of 4-methylbenzophenone (Aldrich), 22.8 g of N-bromosuccinimide (Wako Pure Chemical Industries, Ltd.), 0.54 g of benzoyl peroxide (containing 20% water, Wako Pure Chemical Industries, Ltd.), and 80 g of acetonitrile, which were heated to 80° C. and were made react under reflux for 2 hours. After cooling, the solvent was distilled away and the residue was recrystallized from 160 g of methanol, so that 26 g of intermediate (H10) (white crystals) was obtained. As a result of an analysis by $^1$H-NMR {300 MHz, CDCl$_3$, δ (ppm): 7.9-7.7 (m, 4H), 7.6 (t, 1H), 7.55-7.4 (m, 4H), 4.5 (s, 2H)}, it was confirmed that this intermediate (H10) was 4-bromomethylphenylbenzophenone.

(2) Synthesis of 8-(4-benzoylphenyl)methyl-1,8-diazabicyclo[5.4.0]-7-undecenium bromide (intermediate H11)

In 100 g of acetonitrile was dissolved 25.8 g of intermediate (H10), and 14.6 g of 1,8-diazabicyclo[5.4.0]-7-undecene (San-Apro Ltd.) was dropped thereto (heat was generated after the dropping). After stirring under room temperature (about 25° C.) for 18 hours, acetonitrile was distilled away, so that a brown solid was obtained. This brown solid was dissolve in acetonitrile and recrystallized therefrom, so that 28.2 g of intermediate (H11) (white solid) was obtained. As a result of an analysis by $^1$H-NMR {300 MHz, CDCl$_3$, δ (ppm): 7.9-7.7 (d, 4H), 7.6-7.3 (m, 5H), 5.0 (s, 2H), 3.9-3.6 (m, 6H), 3.0-2.9 (m, 2H), 2.3-2.2 (m, 2H), 1.9-1.7 (m, 6H)}, it was confirmed that this intermediate (H11) was 8-(4-benzoylphenyl)methyl-1,8-diazabicyclo[5.4.0]-7-undecenium bromide.

(3) Synthesis of 8-(4-benzoylphenyl)methyl-1,8-diazabicyclo[5.4.0]-7-undecenium phenylglyoxylate To a solution obtained by dissolving 4.4 g of silver phenylglyoxylate prepared in the same manner as in Example 18 in 40 g of methanol was dropped little by little 6.8 g of intermediate (H11) (8-(4-benzoylphenyl)methyl-1,8-diazabicyclo[5.4.0]-7-undecenium bromide) which had beforehand been dissolved in 60 g of methanol. Then stirring was continued at room temperature (about 25° C.) for 2 hours, so that a reaction liquid was obtained. The reaction liquid was filtered and yellow oil obtained by concentrating the filtrate was dissolved in acetonitrile and recrystallized therefrom, so that 7.6 g of a photobase generator (H1) for comparison (white solid) was obtained. As a result of an analysis by $^1$H-NMR {300 MHz, CDCl$_3$, δ (ppm): 8.1-8.0 (d, 2H), 7.85-7.7 (m, 4H), 7.6 (t, 1H), 7.55-7.3 (m, 7H), 5.0 (s, 2H), 3.9-3.7 (m, 6H), 3.0-2.9 (m, 2H), 2.3-2.1 (m, 2H), 1.9-1.6 (m, 6H)}, it was confirmed that this white solid was 8-(4-bezoylphenyl)methyl-1,8-diazabicyclo[5.4.0]-7-undecenium phenylglyoxylate.

[Chem. 46]

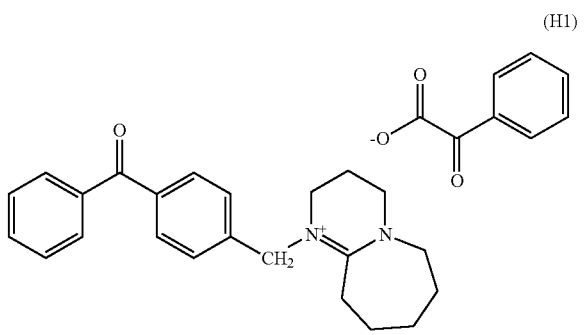

(H1)

Comparative Example 2

Synthesis of 8-(4-phenylthiobezoyl)methyl-1,8-diazabicyclo[5.4.0]-7-undecenium tetraphenylborate {a photobase generator represented by chemical formula (H2)}

In 40 g of diethyl ether was dissolved 1.7 g of 2-bromo-4-phenylthioacetophenone (Aldrich), and then 0.61 g of 1,8-diazabicyclo[5.4.0]-7-undecene (San-Apro Ltd.) was dropped thereto. After stirring at room temperature (about 25° C.) for 30 minutes, a precipitated orange solid was collected by filtration. This orange solid was dissolved in 30 g of ethanol, and a solution composed of 0.97 g of sodium tetraphenylborate (Nacalai Tesque, Inc.) and 30 g of ethanol was added thereto, followed by stirring at room temperature (about 25° C.) for 30 minutes, so that a reaction liquid was obtained. The reaction liquid was filtered and dried, so that 1.75 g of a photobase generator (H2) for comparison (white solid) was obtained. As a result of an analysis by $^1$H-NMR {300 MHz, CD$_3$CN, δ (ppm): 7.8-6.8 (m, 29H), 5.0 (s, 2H), 3.6-3.5 (m, 4H), 3.3 (t, 2H), 2.6-2.5 (m, 2H), 2.2-2.1 (m, 2H), 1.7 (m, 4H), 1.5 (m, 2H)}, it was confirmed that this white solid was 8-(4-phenylthiobezoyl)methyl-1,8-diazabicyclo[5.4.0]-7-undecenium phenylglyoxylate.

[Chem. 47]

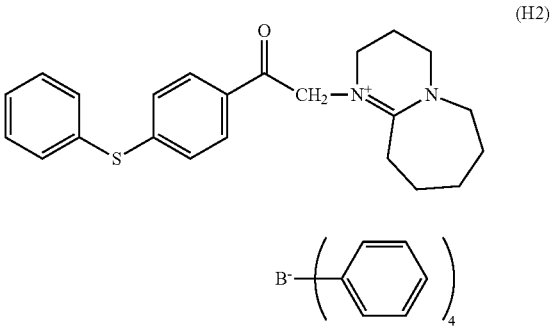

Comparative Example 3

Synthesis of 1-fluorenyl-1-azabicyclo[2.2.2]octanium bromide {a photobase generator represented by chemical formula (H3)}

In 250 g of toluene was dissolved 2.4 g of 9-bromofluorene (Tokyo Chemical Industry Co., Ltd.), and 1.2 g of quinuclidine (Aldrich) was added thereto. After a reaction was performed at room temperature (about 25° C.) for 18 hours, the formed solid was collected by filtration, so that 3.0 g of a photobase generator (H3) for comparison (white solid) was obtained. As a result of an analysis by $^1$H-NMR {300 MHz, DMSO-d6, δ (ppm): 8.0 (d, 2H), 7.9 (d, 2H), 7.6 (t, 2H), 7.4 (t, 2H), 5.7 (s, 1H), 3.5 (t, 6H), 2.0 (m, 1H), 1.9-1.85 (m, 6H)}, it was confirmed that this white solid was 1-fluorenyl-1-azabicyclo[2.2.2]octanium bromide.

[Chem. 48]

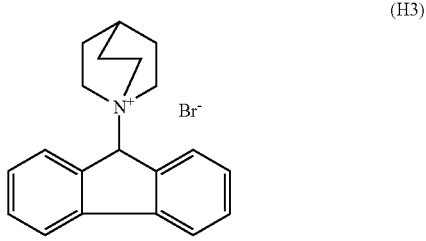

(H3)

<Measurement of Molar Absorption Coefficient of Photobase Generator>

For the photobase generators (1-1) to (2-5) and (H1) to (H3) obtained in Examples and Comparative Examples, molar absorption coefficients ε (365 nm, 405 nm) were measured, and the results are shown in Table 1. It was found that the photobase generators of the present invention (1-1) to (2-5) could absorb lights having wavelengths of 365 nm and 405 nm efficiently. On the other hand, as to the photobase generators for comparison, only a slight absorption was observed at 365 nm.

Measuring Method

About 50 mg of a sample (a photobase generator) was weighed precisely in a 50-mL volumetric flask, and about 20 g of acetonitrile was added thereto to dissolve the sample. Then acetonitrile was added, thereby achieving coincidence with a marked line. A 1-mL portion of this solution was taken into a 20-mL volumetric flask by using a measuring pipet and was diluted by adding acetonitrile to a marked line, so that an acetonitrile solution with a prescribed concentration was obtained. This solution was put into a quartz cell (optical path length: 1 cm), and an absorption spectrum within a wavelength range of 200 to 500 nm was measured by a spectrophotometer (UV-2550, manufactured by Shimadzu Corp.). From an absorbance obtained from the spectrum, a molar absorption coefficient was calculated in accordance with the following formula.

Molar absorption coefficient(ε)=(absorbance)/molar concentration(mol/L)

<Photodegradability of Photobase Generator>

For the photobase generators (1-1) to (2-5) and (H1) to (H3) obtained in Examples and Comparative Examples, a photodegradability test using a dye (bromothymol blue) was carried out, and the results are shown in Table 1. The photobase generators of the present invention exhibited color change (from yellow to blue) which indicated the generation of a base and therefore it was shown that the photobase generators generated bases efficiently. On the other hand, the photobase generators for comparison were not observed to exhibit color change or still exhibited a green color (a color between yellow and blue, which indicates the generation of a very slight amount of base).

Measuring Method

Into a test tube with a screw cap was taken 2 mg of a sample (a photobase generator), which was then dissolved in 8 g of acetonitrile. After being capped hermetically, the test tube was exposed to light while being laid on a belt conveyer of a belt conveyor type UV irradiator (ECS-151U, manufactured by EYE GRAPHICS CO., LTD.). Then, one drop of 0.1% aqueous bromothymol blue solution was added into the test tube.

In order to control an exposure wavelength, a filter capable of allowing light with a wavelength of 300 to 450 nm to pass and blocking light with other wavelengths (365 FILTER, manufactured by EYE GRAPHICS CO., LTD.) or a filter capable of blocking light with a wavelength of 390 nm or less (L39, manufactured by Kenko Kogaku Co., Ltd.) was mounted. The light exposure was about 0.6 J/cm² for 365 nm and about 12 J/cm² for 405 nm. When bases are generated, the color changed to blue and it was expressed by symbol ○. On the other hand, when no base generated, the color remained to yellow and it was expressed by symbol X. Moreover, when a very small amount of base generated, the color changed to green, which is a color between yellow and blue, and it was expressed by symbol Δ.

TABLE 1

|  |  | Photobase generator | Molar absorption coefficient | | Photodegradability | |
|---|---|---|---|---|---|---|
|  |  |  | 365 nm | 405 nm | 365 nm | >400 nm |
| Example | 1 | (1-1) | 4520 | 340 | ○ | ○ |
|  | 2 | (2-2) | 6530 | 7430 | ○ | ○ |
|  | 3 | (2-5) | 7220 | 70 | ○ | X |
|  | 4 | (1-2) | 6140 | 90 | ○ | ○ |
|  | 5 | (1-3) | 2070 | 5500 | ○ | ○ |
|  | 6 | (1-4) | 3270 | 5070 | ○ | ○ |
|  | 7 | (1-5) | 2010 | 3540 | ○ | ○ |
|  | 8 | (1-6) | 2610 | 1070 | ○ | ○ |
|  | 9 | (1-7) | 5430 | 1170 | ○ | ○ |
|  | 10 | (1-8) | 2940 | 6140 | ○ | ○ |
|  | 11 | (2-1) | 7110 | 80 | ○ | ○ |
|  | 12 | (2-3) | 6820 | 780 | ○ | ○ |
|  | 13 | (2-4) | 6780 | 2200 | ○ | ○ |
|  | 14 | (2-6) | 7200 | 80 | ○ | X |
|  | 15 | (2-7) | 7110 | 60 | ○ | X |
|  | 16 | (2-8) | 7100 | 80 | ○ | X |
|  | 17 | (2-9) | 7070 | 70 | ○ | X |
|  | 18 | (2-10) | 7080 | 0 | ○ | X |
|  | 19 | (2-11) | 7070 | 60 | ○ | X |
| Comparative Example | 1 | (H1) | 160 | 0 | Δ | X |
|  | 2 | (H2) | 400 | 0 | Δ | X |
|  | 3 | (H3) | 10 | 0 | X | X |

The photobase generators of the present invention were higher in molar absorption coefficient than the photobase generators for comparison, and they were remarkably high in molar absorption coefficient at 365 nm, especially. Moreover, the photobase generators of the present invention were superior in photodegradability to the photobase generators for comparison, and they were excellent in photodegradability at 365 nm, especially. It therefore is clear that the photobase generators of the present invention generate bases by light (especially, light near 365 nm) more efficiently in comparison to the photobase generators for comparison.

Example 20

One hundred grams of a bisphenol A type epoxy resin (JER-828, produced by Japan Epoxy Resin Co. Ltd.), 90 g of an acid anhydride (HN5500E, produced by Hitachi Chemical Co., Ltd.), and 4.5 g of photobase generator (1-1) (the amount of corresponding DBU: 1 g) were mixed uniformly, applied to a glass substrate (76 mm×52 mm) with a bar coater (No. 10, YASUDA SEIKI SEISAKUSHO, LTD.), and then exposed to light with a belt conveyer type UV irradiator (ECS-151U, manufactured by EYE GRAPHICS CO., LTD.) {a filter capable of allowing light with a wavelength of 300 to 450 nm (365 FILTER, manufactured by EYE GRAPHICS CO., LTD.) was used for controlling the exposure wavelength}, so that a base was generated. Subsequently, it was placed on a hot plate heated to 150° C. and the time required for the applied surface to lose its tackiness was measured. The tackiness was lost in 3 to 4 minutes.

On the other hand, a sample was got applied in the same manner as above except for failing to be exposed to light and then was put on a hot plate heated to 150° C. and the time required for the applied surface to lose its tackiness was measured. The tackiness remained even though 30 minutes had lapsed.

Comparative Example 4

In the same manner as in Example 20 except for changing "4.5 g of photobase generator (1-1) (the amount of corresponding DBU: 1 g)" to "3.1 g of photobase generator (H1) (the amount of corresponding DBU: 1 g)", a sample was put on a hot plate heated to 150° C. and the time required for the applied surface to lose its tackiness. The tackiness was lost in 3 to 4 minutes.

On the other hand, a sample was got applied in the same manner as above except for failing to be exposed to light and then was put on a hot plate heated to 150° C. and the time required for the applied surface to lose its tackiness was measured. The tackiness was lost in 3 to 4 minutes.

Comparative Example 5

In the same manner as in Example 20 except for failing to use "4.5 g of photobase generator (1-1)", a sample was put on a hot plate heated to 150° C. and the time required for the applied surface to lose its tackiness was measured. The tackiness remained even though 30 minutes had lapsed.

On the other hand, a sample was got applied in the same manner as above except for failing to be exposed to light and then was put on a hot plate heated to 150° C. and the time required for the applied surface to lose its tackiness was measured. The tackiness remained even though 30 minutes had lapsed.

As described above, the photobase generators of the present invention generated bases by light effectively to promote curing reactions of epoxy resins efficiently but failed to promote curing reactions of epoxy resins if not being exposed to light even though they were heated. On the other hand, since the photobase generators for comparison generated bases and promoted curing reactions of epoxy resins efficiently with or without being exposed to light, it is conceivable that they do not generate bases effectively by light but they generated bases effectively by heat.

The invention claimed is:

1. A photobase generator represented by general formula (1) or (2):

[Chem. 1]

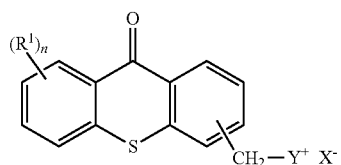

(1)

[Chem. 2]

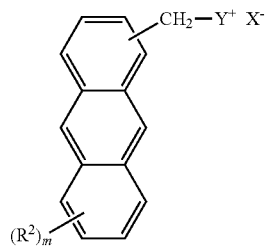

(2)

wherein $R^1$ and $R^2$ are each an alkyl group having from 1 to 18 carbon atoms, an alkenyl group having from 2 to 18 carbon atoms, an alkynyl group having from 2 to 18 carbon atoms, an aryl group having from 6 to 14 carbon atoms, a nitro group, a hydroxyl group, a cyano group, an alkoxy group represented by $-OR^3$, an amino group represented by $-NR^4R^5$, an acyl group represented by $R^6CO-$, an acyloxy group represented by $R^7COO-$, an alkylthio group or an arylthio group represented by $-SR^8$, or a halogen atom, $R^3$, $R^6$, $R^7$, and $R^8$ are each an alkyl group having from 1 to 8 carbon atoms, or an aryl group having from 6 to 12 carbon atoms, $R^4$ and $R^5$ are each a hydrogen atom, an alkyl group having from 1 to 8 carbon atoms, or an aryl group having from 6 to 12 carbon atoms, n is an integer of from 0 to 7, m is an integer of from 0 to 9, $Y^+$ is a quaternary ammonio group represented by any one of general formulae (3) to (6), Q is a nitrogen atom or a methine group ($-CH-$), t and u are each 2 or 3, w is an integer of from 0 to 2, A is a hydrogen atom, a hydroxyl group, or a halogen atom, $R^9$ to $R^{11}$ are each an alkyl group having 1 to 18 carbon atoms, an alkenyl group having 2 to 18 carbon atoms, or an aryl group having 6 to 14 carbon atoms, $R^1$ or $R^2$ and $CH_2-Y^+X^-$ may be attached to the same benzene ring or alternatively may be attached to different benzene rings, and $X^-$ is a counter anion selected from among a borate anion, a phenolate anion, and a carboxylate anion.

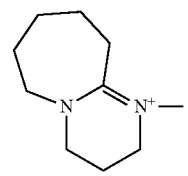

(3)

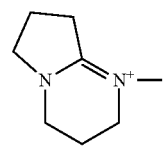

(4)

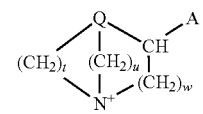

(5)

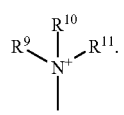

(6)

2. The photobase generator according to claim 1 which is represented by general formula (7), wherein $R^1$ is an alkoxy group having from 1 to 4 carbon atoms and $Y^+$ is a quaternary ammonio group represented by general formula (3) or (4), or which is represented by general formula (8), wherein $Y^+$ is a quaternary ammonio group represented by general formula (3) or (4):

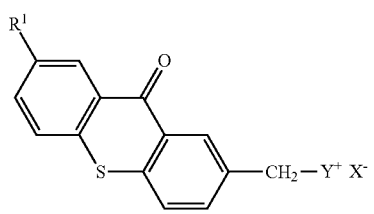
(7)

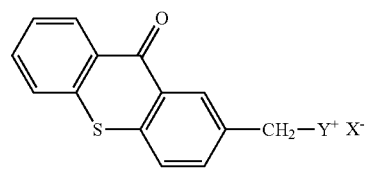
(8)

wherein $X^-$ is a counter anion selected from among a borate anion, a phenolate anion, and a carboxylate anion.

3. The photobase generator according to claim 1 which is represented by general formula (9), wherein $R^1$ is a hydroxyl group, an alkoxy group having from 1 to 4 carbon atoms, or an acetoxy group, and $Y^+$ is a quaternary ammonio group represented by general formula (3) or (4), or which is represented by general formula (10), wherein $Y^+$ is a quaternary ammonio group represented by general formula (3) or (4):

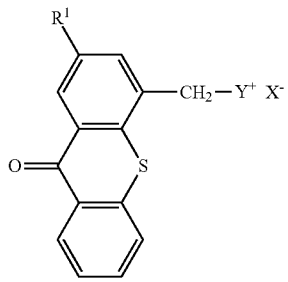
(9)

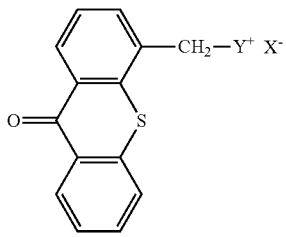
(10)

wherein $X^-$ is a counter anion selected from among a borate anion, a phenolate anion, and a carboxylate anion.

4. The photobase generator according to claim 1 which is represented by general formula (11), wherein $R^2$ is an alkoxy group having from 1 to 4 carbon atoms, an acetyl group, or a benzoyl group, and $Y^+$ is a quaternary ammonio group represented by general formula (3) or (4):

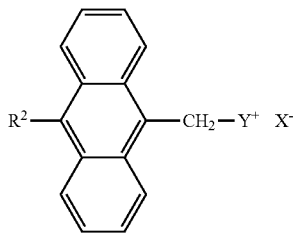
(11)

wherein $X^-$ is a counter anion selected from among a borate anion, a phenolate anion, and a carboxylate anion.

5. The photobase generator according to claim 1, wherein $X^-$ is a tetraphenylborate anion or a phenylglyoxylate anion.

6. A curable resin composition characterized in comprising the photobase generator according to claim 1, a curable urethane resin, a curable epoxy resin, a curable acrylic resin, and/or a polysiloxane.

7. A method for producing a cured resin characterized in comprising a step of generating a base by irradiating the photobase generator contained in the curable resin composition according to claim 6 with light having a wavelength of from 350 to 500 nm.

8. A method for producing a cured resin characterized in comprising a step of generating a base by irradiating the photobase generator contained in the curable resin composition according to claim 6 with light having a wavelength of from 400 to 500 nm.

* * * * *